(12) United States Patent
Fairfax

(10) Patent No.: US 8,859,777 B2
(45) Date of Patent: Oct. 14, 2014

(54) 4-FLUORO-4-ARYLPIPERDIN-1-YL DERIVATIVES AS MU OPIOID FUNCTION MODERATORS

(75) Inventor: David J. Fairfax, Slingerlands, NY (US)

(73) Assignee: Kinentia Biosciences LLC, Rensselaer, NY (US)

( * ) Notice: Subject to any disclaimer, the term of this patent is extended or adjusted under 35 U.S.C. 154(b) by 0 days.

(21) Appl. No.: 13/695,065

(22) PCT Filed: Apr. 29, 2011

(86) PCT No.: PCT/US2011/034533
§ 371 (c)(1),
(2), (4) Date: Oct. 29, 2012

(87) PCT Pub. No.: WO2011/137331
PCT Pub. Date: Nov. 3, 2011

(65) Prior Publication Data
US 2013/0045165 A1    Feb. 21, 2013

Related U.S. Application Data

(60) Provisional application No. 61/330,010, filed on Apr. 30, 2010.

(51) Int. Cl.
| | |
|---|---|
| *C07D 211/08* | (2006.01) |
| *A61K 31/485* | (2006.01) |
| *C07D 489/02* | (2006.01) |
| *C07D 491/18* | (2006.01) |
| *C07D 405/06* | (2006.01) |
| *C07D 211/38* | (2006.01) |
| *A61K 31/445* | (2006.01) |
| *C07D 489/08* | (2006.01) |
| *C07D 221/06* | (2006.01) |
| *C07D 471/08* | (2006.01) |

(52) U.S. Cl.
CPC ............. *A61K 31/445* (2013.01); *A61K 31/485* (2013.01); *C07D 489/02* (2013.01); *C07D 491/18* (2013.01); *C07D 405/06* (2013.01); *C07D 211/38* (2013.01); *C07D 489/08* (2013.01); *C07D 221/06* (2013.01); *C07D 471/08* (2013.01)
USPC ......................................................... 546/192

(58) Field of Classification Search
CPC ...................................................... C07D 211/08
USPC ........................................................ 546/192
See application file for complete search history.

(56) References Cited

U.S. PATENT DOCUMENTS

| | | | |
|---|---|---|---|
| 6,509,346 B2 * | 1/2003 | Luly et al. | ...................... 514/291 |
| 7,541,365 B2 | 6/2009 | Luly et al. | |
| 2002/0119973 A1 | 8/2002 | Luly et al. | |

FOREIGN PATENT DOCUMENTS

| | | | | |
|---|---|---|---|---|
| AU | WO 0248117 | * | 6/2002 | ........... C07D 239/90 |
| WO | WO 0109137 | * | 2/2001 | ........... C07D 491/04 |
| WO | WO 2006058294 | * | 6/2006 | ......... A61K 31/4439 |
| WO | 2008012623 A1 | | 1/2008 | |
| WO | 2009041663 A1 | | 4/2009 | |

OTHER PUBLICATIONS

International Search Report for PCT/US2011/034533 dated Feb. 8, 2012.

* cited by examiner

*Primary Examiner* — Nizal Chandrakumar
(74) *Attorney, Agent, or Firm* — Heslin Rothenberg Farley & Mesiti P.C.

(57) ABSTRACT

4-Fluoro-4-phenylpiperidin-1-yl µ antagonists of general structure

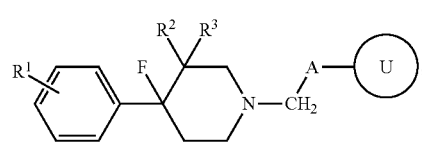

as well as pharmaceutical compositions comprising compounds of formula I, are disclosed. These compounds and compositions are useful as treatments of conditions or diseases associated with binding opioid receptors including pain, obesity, hyperalgesia, inflammation, osteoarthritis, drug addiction, and cancer. These compounds and compositions are also useful as treatments for tardive dyskinesia.

15 Claims, No Drawings

4-FLUORO-4-ARYLPIPERDIN-1-YL DERIVATIVES AS MU OPIOID FUNCTION MODERATORS

CROSS REFERENCE TO RELATED APPLICATIONS

This application is a U.S. National Phase filing under 35 U.S.C. 371 of International Application PCT/US2011/034533, filed Apr. 29, 2011, and published as WO 2011/137331 on Nov. 3, 2011. PCT/US2011/034533 claims priority of U.S. provisional application 61/330,010, filed Apr. 30, 2010. The entire contents of each of the prior applications are hereby incorporated herein by reference.

CROSS REFERENCE TO RELATED APPLICATIONS

This application claims priority of U.S. provisional application 61/330,010, filed Apr. 30, 2010, the entire disclosure of which is incorporated herein by reference.

FIELD OF THE INVENTION

The invention relates to μ opioid receptor binding phenylpiperidine compounds. The compounds are useful in conditions or diseases associated with binding opioid receptors, for instance, as analgesics and tardive dyskinesia treatments.

BACKGROUND OF THE INVENTION

Opiates have been the subject of intense research since the isolation of morphine in 1805, and thousands of compounds having opiate or opiate-like activity have been identified. Many opioid receptor-interactive compounds, including those used for producing analgesia (e.g., morphine) and those used for treating drug addiction (e.g., naltrexone and cyclazocine) in humans work by triggering μ opioid receptors in the central nervous system (CNS) and by crossing the blood-brain barrier. However, as there are μ opioid receptors elsewhere in the body, i.e., peripheral to the CNS and brain, sometimes these opiates can cause unwanted side effects. Often, these side effects target the gastrointestinal (GI) tract; for instance, prolonged morphine administration often causes constipation in patients. Thus, a drug that is able to treat symptoms of pain, for instance, but not stimulate the opioid receptors in the GI tract, would allow for pain relief without intestinal side effects.

SUMMARY OF THE INVENTION

The compounds of the invention are useful as analgesics, anti-pruritics, anti-diarrheal agents, anticonvulsants, antitussives, anorexics and as treatments for hyperalgesia, drug addiction, respiratory depression, dyskinesia, pain (including neuropathic pain), irritable bowel syndrome and gastrointestinal motility disorders. Drug addiction, as used herein, includes heroin, cocaine, nicotine, amphetamine and alcohol addiction. There is evidence in the literature that the compounds may also be useful as immunosuppressants and anti-inflammatories and for reducing ischemic damage (and cardioprotection), for improving learning and memory, and for treating urinary incontinence. Further, a recent article suggests that there is a link between opioids and cancer progression and intimates that opioid receptor compounds may have an effect on tumor progression (Clinical Oncology, March 2010, Vol. 04:03, available at http://www.clinicaloncology.com/index.asp?section_id=150&show=dept&issue_id=615&article_id=14811).

In one aspect, the invention relates to compounds of formula I:

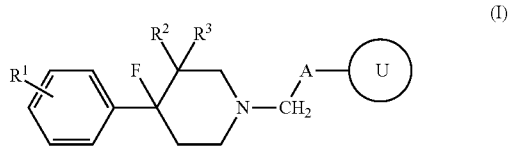

wherein $R^1$ is from one to three substituents chosen independently in each occurrence from hydrogen, halogen, halo($C_1$-$C_6$)alkyl, ($C_1$-$C_6$)alkyl, ($C_1$-$C_6$)acyl, ($C_1$-$C_6$)alkoxy($C_1$-$C_6$)alkyl, hydroxy($C_1$-$C_6$)alkyl, heteroaryl, benzenesulfonyl, toluenesulfonyl, hydroxy, ($C_1$-$C_6$)alkoxy, hydroxy($C_1$-$C_6$)alkoxy, halo($C_1$-$C_6$)alkoxy, ($C_1$-$C_6$)oxaalkyl, carboxy, carboxy($C_1$-$C_6$)alkoxy, ($C_1$-$C_6$)alkoxycarbonyl, ($C_1$-$C_6$)alkoxycarbonylamino, carboxamido, ($C_1$-$C_6$)alkylaminocarbonyl, ($C_1$-$C_6$)alkylaminocarbonyloxy, ($C_1$-$C_6$)alkylaminocarbonylamino, cyano, acetoxy, nitro, amino, ($C_1$-$C_6$)alkylamino, di($C_1$-$C_6$)alkylamino, ($C_1$-$C_6$)alkylamino($C_1$-$C_6$)alkyl, di($C_1$-$C_6$)alkylamino($C_1$-$C_6$)alkyl, di($C_1$-$C_6$)alkylamino($C_1$-$C_6$)alkoxy, mercapto, ($C_1$-$C_6$)alkylthio, ($C_1$-$C_6$)alkylsulfonylamino, benzenesulfonylamino, toluenesulfonylamino, ($C_1$-$C_6$)alkylaminosulfonyl, di($C_1$-$C_6$)alkylaminosulfonyl, ($C_1$-$C_6$)alkylsulfinyl, ($C_1$-$C_6$)alkylsulfonyl, ($C_1$-$C_6$)acylamino, aryl, benzyl, heterocyclyl, heterocyclyl($C_1$-$C_6$)alkyl, phenoxy, benzyloxy, heteroaryloxy, hydroxyimino, ($C_1$-$C_6$)alkoxyimino, oxaalkyl, amidino, and guanidino;

$R^2$ and $R^3$ are independently chosen from hydrogen and ($C_1$-$C_6$)alkyl;

A is a direct bond or a ($C_1$-$C_8$)alkylene chain wherein one or two methylenes may be optionally replaced by oxygen or —$CR^4R^5$—;

$R^4$ and $R^5$ are independently chosen from hydrogen, ($C_1$-$C_{10}$)alkyl, halo($C_1$-$C_6$)alkyl, ($C_1$-$C_6$)acyl, hydroxy($C_1$-$C_6$)alkyl, hydroxy, ($C_1$-$C_6$)alkoxy, hydroxy($C_1$-$C_6$)alkoxy, halo($C_1$-$C_6$)alkoxy, ($C_1$-$C_6$)oxaalkyl, carboxy, ($C_1$-$C_6$)alkoxycarbonyl, ($C_1$-$C_6$)alkoxycarbonylamino, carboxamido, ($C_1$-$C_6$)alkylaminocarbonyl, amino, ($C_1$-$C_6$)alkylamino, di($C_1$-$C_6$)alkylamino, aryl, benzyl, heterocyclyl, heterocyclyl($C_1$-$C_6$)alkyl, phenoxy, benzyloxy and heteroaryloxy; and U is chosen from optionally substituted($C_3$-$C_8$)carbocycle and optionally substituted heterocyclyl.

In another aspect, the invention relates to a pharmaceutical composition comprising at least one compound of the formula above and a pharmaceutically acceptable carrier.

In another aspect, the invention relates to a method for treating a condition or disease associated with binding opioid receptors in a patient in need thereof, comprising the step of administering to a patient a composition comprising an effective amount of a compound of the formula above. In one embodiment, the disease or condition may be pain, obesity, hyperalgesia, inflammation, osteoarthritis, drug addiction and cancer. In another embodiment, the condition may be tardive dyskinesia.

In another aspect, the invention relates to a compound of formula II:

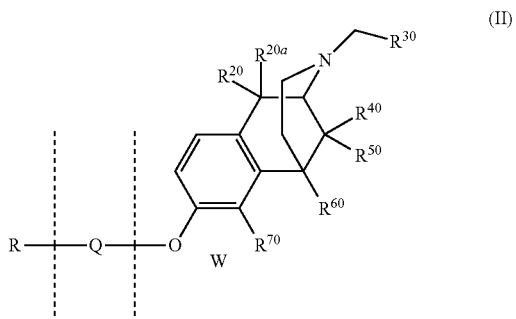

(II)

wherein

W is a CNS-penetrant μ-opioid agonist residue in which $R^{20}$ and $R^{20a}$ are both hydrogen or taken together $R^{20}$ and $R^{20a}$ are =O;

$R^{30}$ is chosen from hydrogen, lower alkyl, alkenyl, aryl, heterocyclyl, benzyl and hydroxyalkyl;

$R^{40}$ is chosen from hydrogen, hydroxy, amino, lower alkoxy, $C_1$-$C_{20}$ alkyl and $C_1$-$C_{20}$ alkyl substituted with hydroxy or carbonyl;

$R^{50}$ is lower alkyl;

$R^{60}$ is lower alkyl;

$R^{70}$ is chosen from hydrogen and hydroxy; or together $R^{40}$, $R^{50}$, $R^{60}$ and $R^{70}$ may form from one to five rings, said rings having optional additional substitution;

R is a CNS-nonpenetrant μ-opioid antagonist residue attached to Q via nitrogen, oxygen or carbonyl; and Q is a ($C_1$-$C_6$)alkylene chain wherein one or two methylenes may be optionally replaced by oxygen or —C(=O)— or, when R is attached by carbonyl, Q may also be a direct bond.

DETAILED DESCRIPTION OF THE INVENTION

A key novel element of the compounds of this invention is the incorporation of a fluorine atom at the 4-position of the piperidine ring. The installation of fluorine into small molecule drugs can greatly enhance the pharmacokinetic and physicochemical properties such as improved metabolic stability and enhanced membrane permeation. [*J. Enzyme Inhibition Medicinal Chem.* (2007), 22, 527-540]. A further application of the fluorine atom is the use of $^{18}$F as a radiolabel tracer atom in the technique of Positron Emission Tomography imaging. Furthermore, a common limitation of piperidine-containing molecules in drug development is the high basicity of the ring nitrogen, resulting in strong ion pairing on exposure to strong acids (such as hydrochloric acid as found in the stomach) and as a result poor oral bioavailability is observed. For example, the development of LY255582, a piperidine based Mu opioid antagonist, as an anti-obesity agent was ceased due to very poor oral bioavailability. [*Bioorg. Medicinal Chem. Lett.* (2007), 17, 6841-6846]. It is contended that, as the incorporation of fluorine into the compounds of this invention greatly reduces the basic nature of the piperidine nitrogen, it is non-obvious that the compounds of the invention would have affinity for the Mu opioid receptor. Additionally, the compounds of the invention have clear pharmacokinetic and diagnostic advantages over existing piperidine-based opioid ligands.

In one aspect, the invention relates to compounds of formula I:

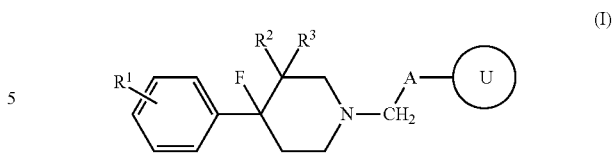

(I)

In some aspects of the invention, $R^1$ can represent one substituent. In other aspects, $R^1$ represents two substituents. In still other aspects, $R^1$ represents three substituents. In the cases where $R^1$ represents two or three substituents, each substituent is chosen independently; that is, one could have both a halogen and a hydroxy substituting the phenyl. In each occurrence, $R^1$ can represent hydrogen, halogen, halo($C_1$-$C_6$)alkyl, ($C_1$-$C_6$)alkyl, ($C_1$-$C_6$)acyl, ($C_1$-$C_6$)alkoxy($C_1$-$C_6$)alkyl, hydroxy($C_1$-$C_6$)alkyl, heteroaryl, benzenesulfonyl, toluenesulfonyl, hydroxy, ($C_1$-$C_6$)alkoxy, hydroxy($C_1$-$C_6$)alkoxy, halo($C_1$-$C_6$)alkoxy, ($C_1$-$C_6$)oxaalkyl, carboxy, carboxy($C_1$-$C_6$)alkoxy, ($C_1$-$C_6$)alkoxycarbonyl, ($C_1$-$C_6$)alkoxycarbonylamino, carboxamido, ($C_1$-$C_6$)alkylaminocarbonyl, ($C_1$-$C_6$)alkylaminocarbonyloxy, ($C_1$-$C_6$)alkylaminocarbonylamino, cyano, acetoxy, nitro, amino, ($C_1$-$C_6$)alkylamino, di($C_1$-$C_6$)alkylamino, ($C_1$-$C_6$)alkylamino($C_1$-$C_6$)alkyl, di($C_1$-$C_6$)alkylamino($C_1$-$C_6$)alkyl, di($C_1$-$C_6$)alkylamino($C_1$-$C_6$)alkoxy, mercapto, ($C_1$-$C_6$)alkylthio, ($C_1$-$C_6$)alkylsulfonylamino, benzenesulfonylamino, toluenesulfonylamino, ($C_1$-$C_6$)alkylaminosulfonyl, di($C_1$-$C_6$)alkylaminosulfonyl, ($C_1$-$C_6$)alkylsulfinyl, ($C_1$-$C_6$)alkylsulfonyl, ($C_1$-$C_6$)acylamino, aryl, benzyl, heterocyclyl, heterocyclyl($C_1$-$C_6$)alkyl, phenoxy, benzyloxy, heteroaryloxy, hydroxyimino, ($C_1$-$C_6$)alkoxyimino, oxaalkyl, amidino, or guanidine.

In some aspects of the invention, $R^1$ is hydrogen. In some aspects of the invention, $R^1$ is halogen. In some of these aspects, $R^1$ is chlorine. In other aspects of the invention, $R^1$ is fluorine. In some of these aspects, the fluorine or chlorine is in the para position relative to the attachment of the piperidine. In some aspects of the invention, $R^1$ is hydroxy. In some of these aspects, the hydroxy is in the para or meta position relative to the attachment of the piperidine. In some aspects of the invention, $R^1$ is ($C_1$-$C_6$)alkoxy. In some aspects of the invention, $R^1$ is carboxy($C_1$-$C_6$)alkoxy. In some aspects of the invention, $R^1$ is carboxymethoxy. In some aspects of the invention, $R^1$ is amino. In some aspects of the invention, $R^1$ is toluenesulfonylamino. In some aspects of the invention, $R^1$ is ($C_1$-$C_6$)alkylsulfonylamino. In some of these aspects, $R^1$ is methylsulfonylamino. In some aspects of the invention, $R^1$ is ($C_1$-$C_6$)alkylaminocarbonyloxy. In some of these aspects, $R^1$ is ethylaminocarbonyloxy. In some aspects of the invention, $R^1$ is ($C_1$-$C_6$)alkylaminocarbonylamino. In some of these aspects, $R^1$ is t-butylaminocarbonylamino. In some aspects of the invention, $R^1$ is hydroxy($C_1$-$C_6$)alkoxy. In some of these aspects, $R^1$ is hydroxyethoxy.

In some aspects of the invention, $R^2$ is hydrogen. In some aspects of the invention, $R^2$ is ($C_1$-$C_6$)alkyl. In some aspects of the invention, $R^3$ is hydrogen. In some aspects of the invention, $R^3$ is ($C_1$-$C_6$)alkyl. In some aspects of the invention, $R^2$ is hydrogen and $R^3$ is hydrogen. In other aspects of the invention, $R^2$ is hydrogen and $R^3$ is ($C_1$-$C_6$)alkyl.

In some aspects of the invention, A is a direct bond. In some aspects of the invention, A is a ($C_1$-$C_8$)alkylene chain. In some aspects of the invention when A is a ($C_1$-$C_8$)alkylene chain, one, two or three methylenes may be optionally replaced by —$CR^4R^5$—. For instance, A may be —$C(R^4R^5)$—, —$C(R^4R^5)C(R^6R^7)$— or —$C(R^4R^5)C(R^6R^7)$ $C(R^8R^9)$—. In some aspects of the invention when A is a $(C_1-C_8)$alkylene chain, one, two or three methylenes may be optionally replaced by oxygen. For instance, A may be —$C(R^4R^5)O$— or $C(R^4R^5)C(R^6R^7)O$—. In some aspects of the invention, A is chosen from —$C(R^4R^5)C(R^6R^7)$— and —$C(R^4R^5)O$—.

In some aspects of the invention, $R^4$ and $R^5$ are independently chosen from hydrogen, $(C_1-C_{10})$alkyl, halo$(C_1-C_6)$alkyl, $(C_1-C_6)$acyl, hydroxy$(C_1-C_6)$alkyl, hydroxy, $(C_1-C_6)$alkoxy, hydroxy$(C_1-C_6)$alkoxy, halo$(C_1-C_6)$alkoxy, $(C_1-C_6)$oxaalkyl, carboxy, $(C_1-C_6)$alkoxycarbonyl, $(C_1-C_6)$alkoxycarbonylamino, carboxamido, $(C_1-C_6)$alkylaminocarbonyl, amino, $(C_1-C_6)$alkylamino, di$(C_1-C_6)$alkylamino, aryl, benzyl, heterocyclyl, heterocyclyl$(C_1-C_6)$alkyl, phenoxy, benzyloxy and heteroaryloxy. In some embodiments, $R^4$, $R^5$, $R^6$, $R^7$, $R^8$ and $R^9$ may each independently be hydrogen, hydroxy, carboxy, $(C_1-C_{10})$alkyl, aryl or benzyl. In these cases, no more than two of $R^4$, $R^5$, $R^6$, $R^7$, $R^8$ and $R^9$ are other than hydrogen.

In some embodiments, A is —$CH_2CH_2$—. In some embodiments, A is —$CH_2O$—. In other embodiments, A is —$CH_2CH_2CH_2$—. In still other embodiments, A is

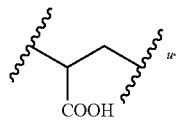

In some embodiments, A is

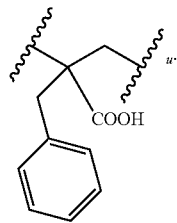 [SMILES: *CC(*)(Cc1ccccc1)C(=O)O]

In yet other embodiments, A is

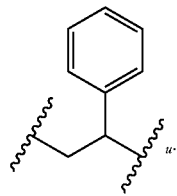

In other embodiments, A is

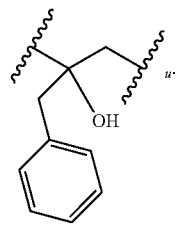 [SMILES: *CC(*)(O)Cc1ccccc1]

In some embodiments, A is

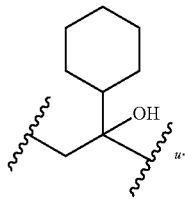 [SMILES: *CC(*)(O)C1CCCCC1]

In some embodiments, A is

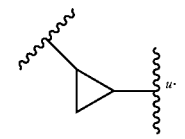

In all of these examples, u indicates the point of attachment to U.

In some embodiments, U is optionally substituted $(C_3-C_8)$ carbocycle. In some of these embodiments, U is optionally substituted phenyl. In other embodiments, U is optionally substituted cyclohexyl. In other embodiments, U is optionally substituted heterocyclyl. In some of these embodiments, U is optionally substituted thiophene. In some of these embodiments, U is optionally substituted furanyl. Examples of substitution for these U rings include hydrogen, halogen, halo$(C_1-C_6)$alkyl, $(C_1-C_6)$alkyl, cyano, acetoxy, $(C_1-C_6)$alkylthio, aryl, aryl$(C_1-C_6)$alkyl, heterocyclyl, heterocyclyl$(C_1-C_6)$alkyl, phenoxy, benzyloxy, aryloxy and heteroaryloxy. U may be optionally substituted by more than one substituent; for instance, the substituent may be only methyl, or two substituents may be methyl and phenyl.

In some aspects of the invention, $R^1$ is chosen from hydrogen, chlorine, fluorine, hydroxy, carboxymethoxy, amino, toluenesulfonylamino, methylsulfonylamino, ethylaminocarbonyloxy, t-butylaminocarbonylamino and hydroxyethoxy; $R^2$ and $R^3$ are independently chosen from hydrogen and $(C_1-C_6)$alkyl; A is chosen from a direct bond, —$C(R^4R^5)C(R^6R^7)$—, —$C(R^4R^5)O$— and —$C(R^4R^5)C(R^6R^7)C(R^8R^9)$—; U is chosen from optionally substituted phenyl, cyclohexyl, thiophene and furanyl; and $R^4$, $R^5$, $R^6$, $R^7$, $R^8$ and $R^9$ are independently chosen from hydrogen, hydroxy, carboxy, $(C_1-C_{10})$alkyl, aryl and benzyl. In these instances, no more than two of $R^4$, $R^5$, $R^6$, $R^7$, $R^8$ and $R^9$ are other than hydrogen.

In another embodiment of the invention, $R^1$ is chosen from chlorine in the para position and hydroxy in the para or meta position, each position relative to the attachment of the piperidine; $R^2$ is hydrogen; $R^3$ is chosen from hydrogen and methyl; A is chosen from —$CH_2CH_2$—, —$CH_2O$—, —$CH_2CH_2CH_2$—,

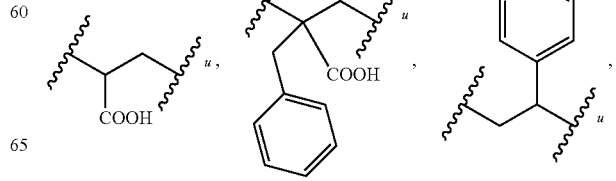

-continued

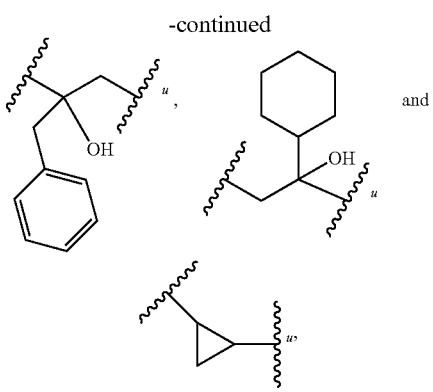

wherein u indicates the point of attachment to U; and U is chosen from phenyl, cyclohexyl, thiophene and furanyl.

One embodiment of the invention relates to a compound

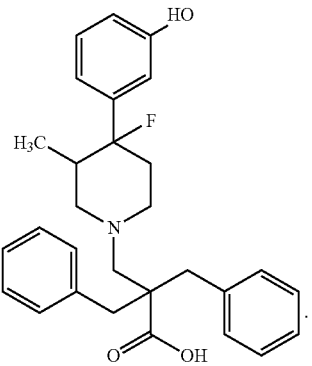 [SMILES: CC1CN(CC(Cc2ccccc2)(Cc2ccccc2)C(=O)O)CCC1(F)c1cccc(O)c1]

Another embodiment of the invention relates to a compound of

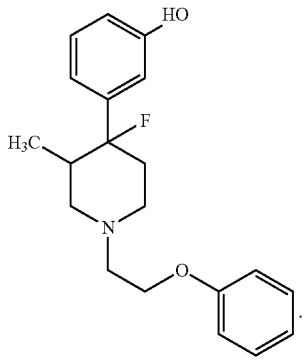 [SMILES: CC1CN(CCOc2ccccc2)CCC1(F)c1cccc(O)c1]

In one embodiment, the invention relates to a compound of formula

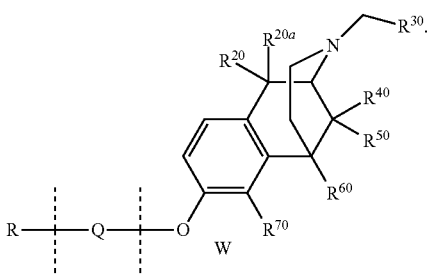

In some embodiments, W is a CNS-penetrant μ-opioid agonist residue.

In some embodiments, $R^{20}$ and $R^{20a}$ are both hydrogen. In other embodiments, $R^{20}$ and $R^{20a}$ are taken together and are =O.

In some embodiments, $R^{30}$ is hydrogen. In some embodiments, $R^{30}$ is lower alkyl. In other embodiments, $R^{30}$ is alkenyl. In some embodiments, $R^{30}$ is aryl. In still other embodiments, $R^{30}$ is heterocyclyl. In some embodiments, $R^{30}$ is benzyl. In other embodiments, $R^{30}$ is hydroxyalkyl.

In some embodiments, $R^{40}$ is hydrogen. In some embodiments, $R^{40}$ is hydroxy. In some embodiments, $R^{40}$ is amino. In some embodiments, $R^{40}$ is lower alkoxy. In some embodiments, $R^{40}$ is $C_1$-$C_{20}$ alkyl. In some embodiments, $R^{40}$ is $C_1$-$C_{20}$ alkyl substituted with hydroxy. In some embodiments, $R^{40}$ is $C_1$-$C_{20}$ alkyl substituted with carbonyl.

In some embodiments, $R^{50}$ is lower alkyl.

In some embodiments, $R^{60}$ is lower alkyl.

In some embodiments, $R^{70}$ is hydrogen. In other embodiments, $R^{70}$ is hydroxy.

In still other embodiments, $R^{40}$, $R^{50}$, $R^{60}$ and $R^{70}$ may form one optionally substituted ring. In yet other embodiments, $R^{40}$, $R^{50}$, $R^{60}$ and $R^{70}$ may form two optionally substituted rings. In further embodiments, $R^{40}$, $R^{50}$, $R^{60}$ and $R^{70}$ may form three optionally substituted rings. In other embodiments, $R^{40}$, $R^{50}$, $R^{60}$ and $R^{70}$ may form four optionally substituted rings. In still other embodiments, $R^{40}$, $R^{50}$, $R^{60}$ and $R^{70}$ may form five optionally substituted rings.

In some embodiments of the invention, R is a CNS-nonpenetrant μ-opioid antagonist residue attached to Q via nitrogen. In other embodiments of the invention, R is a CNS-nonpenetrant μ-opioid antagonist residue attached to Q via oxygen. In other embodiments of the invention, R is a CNS-nonpenetrant μ-opioid antagonist residue attached to Q via carbonyl. In still other embodiments of the invention, R is a residue of a compound of formula I

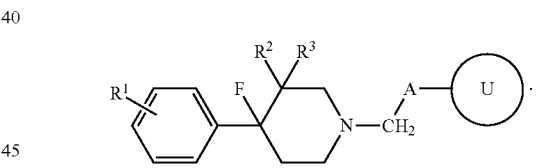

In some embodiments of the invention, Q is a ($C_1$-$C_6$) alkylene chain. In some embodiments, one methylene may be replaced by oxygen. In some embodiments, one methylene may be replaced by —C(=O)—. In some embodiments, two methylenes may be each replaced by oxygen. In some embodiments, two methylenes may be each replaced by —C(=O)—. In still other embodiments, one methylene may be replaced by oxygen and another methylene may be replaced by —C(=O)—. In those embodiments when R is attached by carbonyl, Q may also be a direct bond.

The term "a residue of a compound", when used to describe "R", refers to a compound of formula I minus the functional groups that may be considered part of "Q". For example, in the molecule illustrated below:

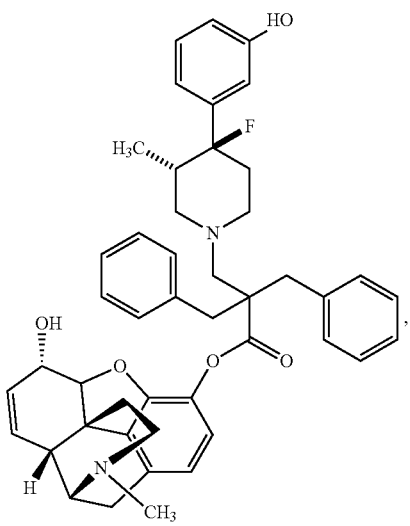

"W" would be represented by

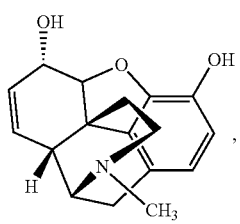

while the parent compound of the "R" residue would be represented by the structure

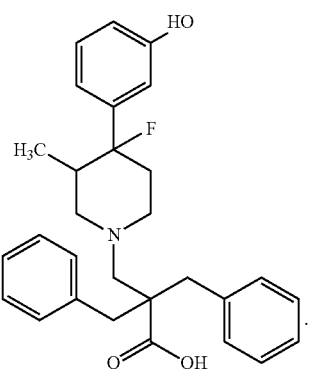 [SMILES: CC1CN(CC(Cc2ccccc2)(Cc2ccccc2)C(=O)O)CCC1(F)c1cccc(O)c1]

As is clear in this instance, an H—O—H is removed from the linkage of the "R" carbonyl and the phenolic OH of "W", while "Q" is a direct bond (as may be the case when R is a carbonyl). Therefore, R becomes a residue of the parent compound shown above. This and similar structures of formula I that may lose some atoms at the points of attachment of "Q" to "R" are referred to herein as "a residue of a compound".

Examples of CNS-penetrant μ-opioid agonist residues that could be represented by "W" include the following compounds in Charts 1, 2 and 3.

Chart 1. Opioid Receptor Ligands
Benzomorphinans (a.k.a. 2,6-Methano-3-benzazocines)

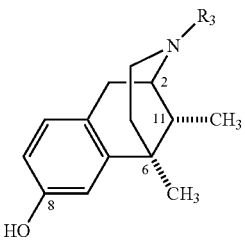

Cyclazocine, $R_3 = CH_2\text{-}c\text{-}C_3H_5$
Metazocine, $R_3 = CH_3$
Phenazocine, $R_3 = CH_2C_6H_5$
SKF 10,047, $R_3 = CH_2CH=CH_2$
Pentazocine, $R_3 = CH_2CH=C(CH_3)_2$
(all racemic)

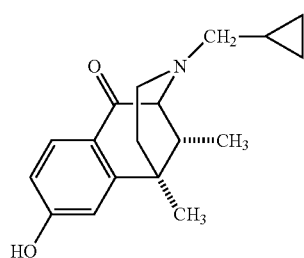

Ketocyclazocine

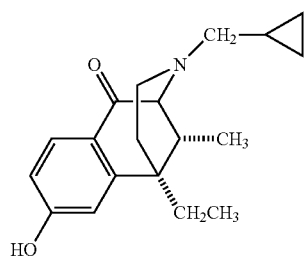

Ethylketocyclazocine (EKC)

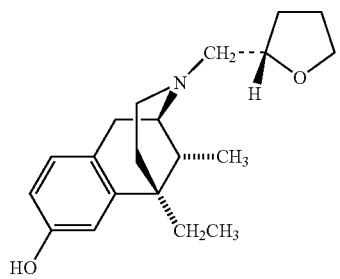

MR2034 - "Merz" core
structure (opt. active)

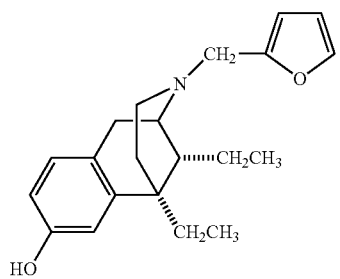

MR2266

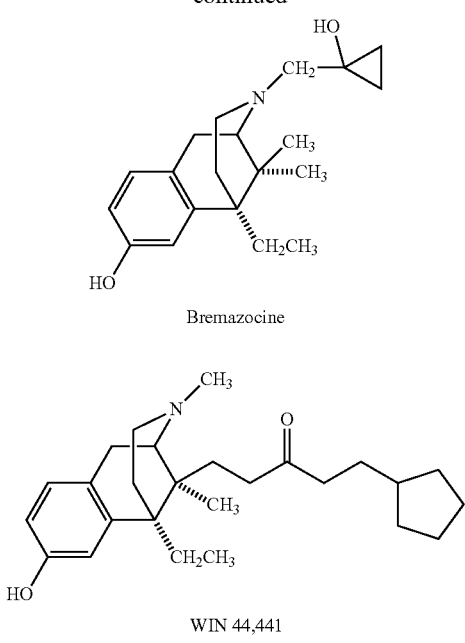
Bremazocine
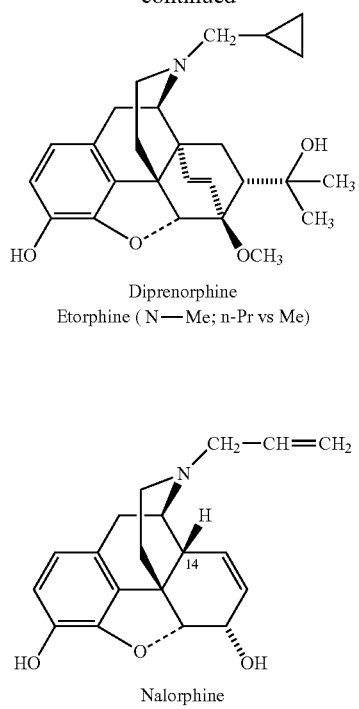
Diprenorphine
Etorphine (N—Me; n-Pr vs Me)
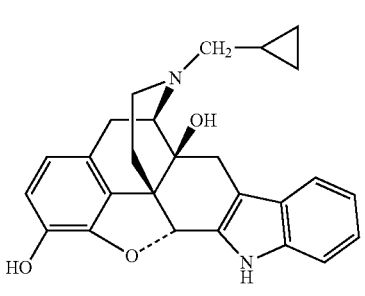
Nalorphine
WIN 44,441
Chart 2. Opioid Receptor Ligands Morphine and Morphinans
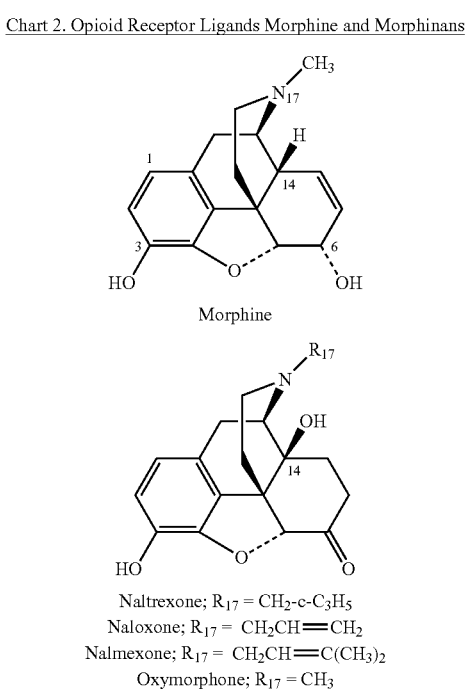
Morphine
Naltrexone; $R_{17}$ = $CH_2$-c-$C_3H_5$
Naloxone; $R_{17}$ = $CH_2CH$=$CH_2$
Nalmexone; $R_{17}$ = $CH_2CH$=$C(CH_3)_2$
Oxymorphone; $R_{17}$ = $CH_3$
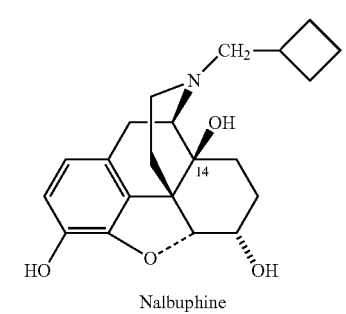
Naltrindole
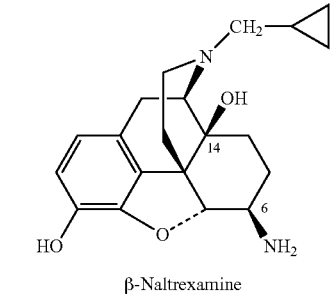
Nalbuphine
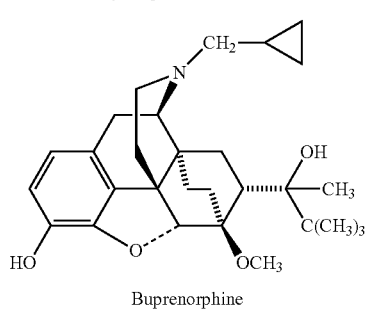
Buprenorphine
β-Naltrexamine

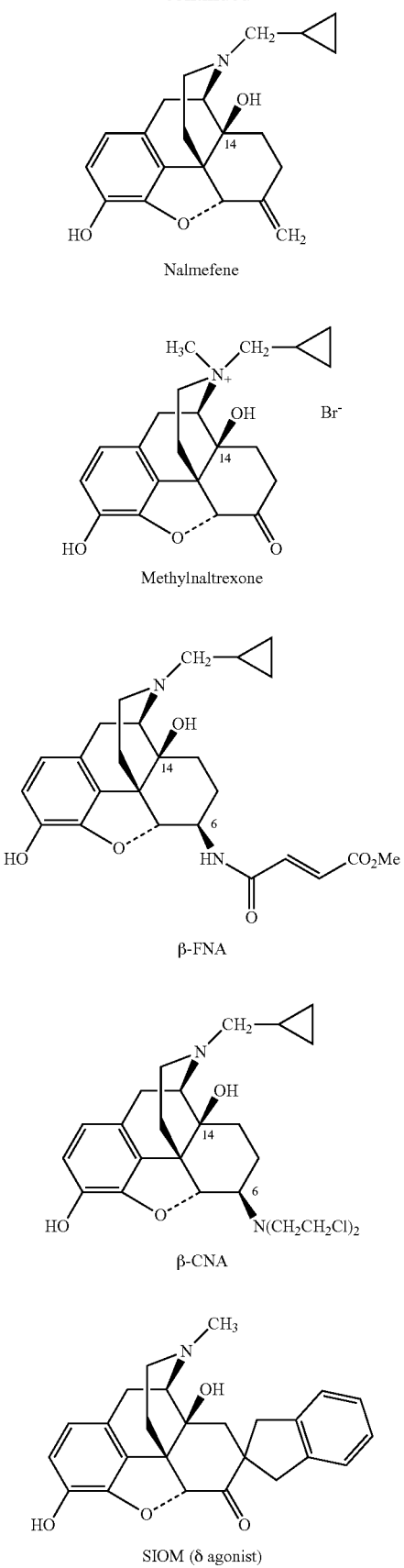
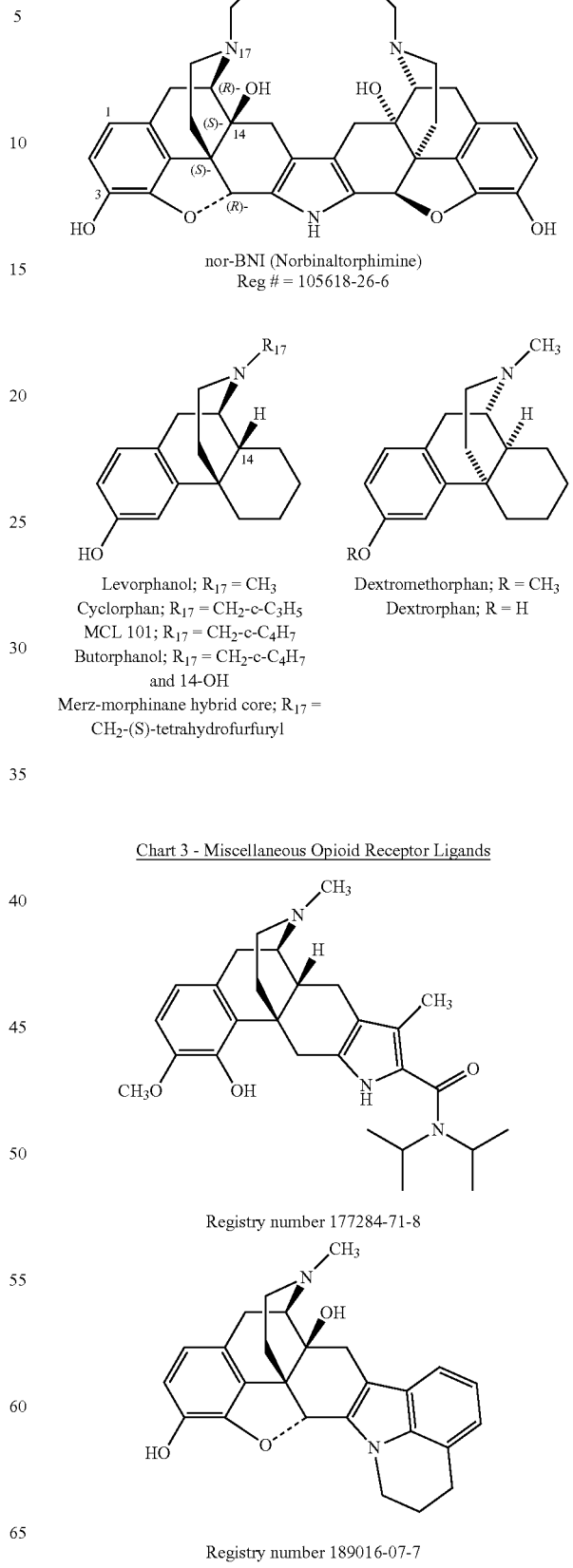

-continued

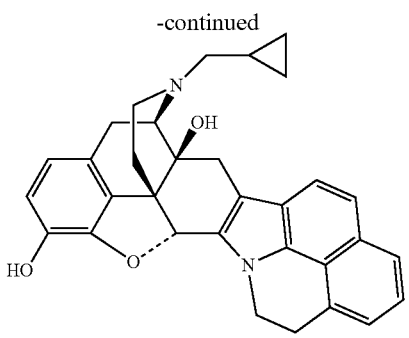

Registry number 189015-08-5

Other opioid receptor ligands are described in Aldrich, J. V. "Analgesics" in *Burger's Medicinal Chemistry and Drug Discovery*, M. E. Wolff ed., John Wiley & Sons 1996, pages 321-44, the disclosures of which are incorporated herein by reference.

DEFINITIONS

Throughout this specification the terms and substituents retain their definitions.

Alkyl is intended to include linear or branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like. To be perfectly clear, for purposes of this application, when A is $(C_1-C_8)$alkylene, it is meant that it can be a straight chain (for instance, methylene or ethylene), a branched chain (e.g., t-butylene), a cycloalkylene (for instance, cyclopropylene or cyclobutylene), or a combination (e.g., methylenecyclopropylene).

Alkoxy or alkoxyl refers to groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

$C_1$ to $C_{20}$ hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, camphoryl and naphthylethyl.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Heterocycle means a cycloalkyl or aryl residue in which one to two of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

As used herein, anti-addition medications can be used interchangeably with the term drug addiction, which includes alcohol, cocaine, heroine, amphetamine and nicotine addiction.

Many of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Some of the compounds of the invention are quaternary salts, i.e. cationic species. Therefore they will always be presented as salts, and the term "pharmaceutically acceptable salt" refers to salts whose counter ion (anion) derives from pharmaceutically acceptable non-toxic acids including inorganic acids, organic acids and water (which formally furnishes the hydroxide anion). Suitable pharmaceutically acceptable anions for the compounds of the present invention include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. The desired salt may be obtained by ion exchange of whatever counter ion is obtained in the synthesis of the quat. These methods are well known to persons of skill. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates. When the compounds of the invention are bisquats, one may employ as counter ions either two monoanionic species (e.g. $Cl_2$) or a single dianionic species (e.g. fumarate). Similarly, one could employ oligoanionic species and make salts having appropriate ratios of quat to counterion, such as (quat)$_3$ citrates. These would be obvious equivalents.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. For instance, the 4-fluorine could easily be substituted by $^{18}F$. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

ABBREVIATIONS

The following abbreviations and terms have the indicated meanings throughout:

Ac=acetyl
Boc=t-butyloxy carbonyl
Bu=butyl
c-=cyclo
DCM=dichloromethane=methylene chloride=$CH_2Cl_2$
DMF=N,N-dimethylformamide
DMSO=dimethyl sulfoxide
EtOAc=ethyl acetate
EtOH=ethanol
GC=gas chromatography
HOAc=acetic acid
Me=methyl
MOR=mu opioid receptor
MTBE=methyl t-butyl ether
PEG=polyethylene glycol
Ph=phenyl
PhOH=phenol
rt=room temperature
sat'd=saturated
s-=secondary
t- or tert-=tertiary
TBDMS=t-butyldimethylsilyl
TFA=trifluoroacetic acid
THF=tetrahydrofuran
TMS=trimethylsilyl
tosyl=p-toluenesulfonyl It may happen that residues in the substrate of interest require protection and deprotection during the conversion of the phenol to the desired Q. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is below, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference.

EXAMPLES

Example 1

Preparation of 4-(4-Chlorophenyl)-1-(3,3-diphenylpropyl)-4-fluoropiperidine Hydrochloride

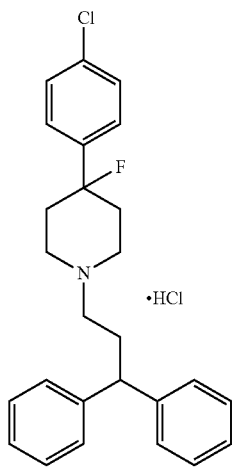 [SMILES: FC1(c2ccc(Cl)cc2)CCN(CCC(c2ccccc2)c2ccccc2)CC1 ; Cl]

Step 1: Preparation of tert-Butyl 4-(4-Chlorophenyl)-4-hydroxypiperidine-1-carboxylate. To a solution of 4-(4-chlorophenyl)-4-hydroxypiperidine (1.75 g, 8.22 mmol) in methylene chloride (100 mL) was added di-tert-butyldicarbonate (1.98 g, 9.10 mmol) followed by diisopropylethylamine (1.17 g, 9.10 mmol) and the resulting solution stirred at room temperature for 6 hours. After this time the reaction was quenched by the addition of 25% aqueous ammonium chloride (250 mL) and the layers separated. The organic layer was washed with water (100 mL) and brine (100 mL) and dried over magnesium sulfate. Subsequent filtration and concentration under reduced pressure afforded tert-butyl 4-(4-chlorophenyl)-4-hydroxypiperidine-1-carboxylate in 81% yield as a viscous clear oil which solidified on standing.

$^1$H NMR (CDCl$_3$): δ=7.41 (d, J=6.8 Hz, 2H), 7.32 (d, J=6.8 Hz, 2H), 3.99 (m, 2H), 3.22 (m, 2H), 2.15 (bs, 1H), 1.94 (dd, J=12.1, 9.5 Hz, 2H), 1.70 (bd, J=14.4 Hz, 2H) and 1.47 ppm (s, 9H).

Step 2: Preparation of 4-(4-Chlorophenyl)-4-fluoropiperidine Hydrochloride. To a solution of tert-butyl 4-(4-chlorophenyl)-4-hydroxypiperidine-1-carboxylate (2.00 g, 6.40 mmol) in methylene chloride (100 mL) was cooled in an ice/salt bath and a solution of diethylaminosulfur trifluoride (1.24 g, 7.68 mmol) in methylene chloride (10 mL) added drop-wise over 1 hour. The resulting solution was then stirred for 14 hours during which time it slowly warmed to room temperature. After this time the reaction was quenched by the cautious addition of saturated sodium bicarbonate (50 mL) and the layers separated. The aqueous layer was extracted with ethyl acetate (50 mL) and the combined organics dried over magnesium sulfate. Subsequent filtration and concentration under reduced pressure afforded crude tert-butyl 4-(4-chlorophenyl)-4-fluoropiperidine-1-carboxylate as a viscous yellow oil. This material was immediately dissolved in 10% methanolic hydrogen chloride (100 mL) and the resulting yellow solution stirred at room temperature for 64 hours then concentrated under reduced pressure. The resulting dark yellow oil was triturated with ethyl acetate (100 mL) for 4 hours after which time a white crystalline solid resulted. This material was isolated by filtration and vacuum dried for 3 hours to afford 4-(4-chlorophenyl)-4-fluoropiperidine hydrochloride in 73% overall yield.

$^1$H NMR (CDCl$_3$): δ=9.81 (bs, 2H), 7.35 (s, 4H), 3.54 (bd, J=10.6 Hz, 2H), 3.32 (m, 2H), 2.66 (m, 1H), 2.58 (m, 1H), 2.13 (m, 1H) and 2.13 ppm (d, J=14.4 Hz, 2H).

Step 3: Preparation of 4-(4-Chlorophenyl)-1-(3,3-diphenylpropyl)-4-fluoropiperidine Hydrochloride. A solution of 4-(4-chlorophenyl)-4-fluoropiperidine hydrochloride (100 mg, 0.40 mmol) and 3,3-diphenyl-1-iodopropane (145 mg, 0.45 mmol) in DMF (2.5 mL) was treated with potassium carbonate (560 mg, 4.05 mmol) and the resulting suspension heated at 80° C. for 14 hours. After this time the reaction was cooled to room temperature and quenched by pouring into 25% aqueous ammonium chloride solution (20 mL). The resulting suspension was then extracted with ethyl acetate (2×10 mL) and the combined extracts washed with water (10 mL) and brine (10 mL) then dried over magnesium sulfate. Subsequent filtration and concentration under reduced pressure afforded crude 4-(4-chlorophenyl)-1-(3,3-diphenyl-propyl)-4-fluoropiperidine as a yellow oil. This material was treated with 10% methanolic hydrogen chloride (10 mL) and the solution concentrated under reduced pressure. Trituration of the resulting oil with 1:1 ethyl acetate/2-butanone (10 mL) afforded a solid which was isolated by filtration and vacuum dried. This afforded a 41% yield of 4-(4-chlorophenyl)-1-(3,3-diphenylpropyl)-4-fluoropiperidine hydrochloride as an off-white solid.

$^1$H NMR (CDCl$_3$): δ=12.6 (bs, 1H), 7.37 (s, 4H), 7.35-7.20 (m, 10H), 4.03 (t, J=7.7 Hz, 1H), 3.58 (bd, J=8.0 Hz, 1H), 3.47 (m, 1H), 3.31 (m, 1H), 3.11 (m, 2H), 2.95 (m, 2H), 2.76 (m, 2H), 2.55 (m, 1H) and 2.13 ppm (dd, J=21.9, 8.3 Hz, 2H). Mass Spectrum: m/z=408 [M+H]$^+$ Example 2

Preparation of 4-(4-Chlorophenyl)-4-fluoro-1-(2-phenoxyethyl)-piperidine Hydrochloride

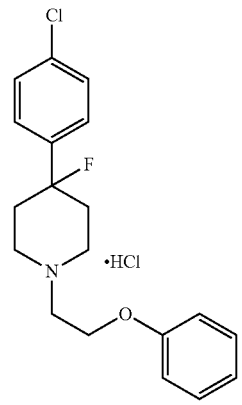 [SMILES: FC1(c2ccc(Cl)cc2)CCN(CCOc2ccccc2)CC1 ; Cl]

The title compound was obtained by the alkylation of 4-(4-chlorophenyl)-4-fluoropiperidine hydrochloride with 1-bromo-2-phenoxyethane and subsequent salt formation with methanolic hydrogen chloride as described in Step 3 of Example 1 in 64% overall yield.

$^1$H NMR (CDCl$_3$): δ=13.2 (bs, 1H), 7.39 (s, 4H), 7.33 (m, 2H), 7.04 (t, J=7.3 Hz, 1H), 6.93 (d, J=8.0 Hz, 2H), 4.61 (bs,

2H), 3.71 (bd, J=10.6 Hz, 2H), 3.51 (m, 2H), 3.37 (dd, J=22.0, 10.3 Hz, 2H), 3.12 (m, 1H), 2.99 (m, 1H) and 2.16 ppm (m, 2H). Mass Spectrum: m/z=334 [M+H]$^+$ Example 3

Preparation of 4-(4-Chlorophenyl)-4-fluoro-1-(3-phenylpropyl)piperidine Hydrochloride

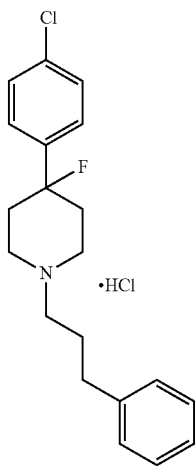 [SMILES: FC1(c2ccc(Cl)cc2)CCN(CCCc2ccccc2)CC1 ; Cl]

The title compound was obtained by the alkylation of 4-(4-chlorophenyl)-4-fluoropiperidine hydrochloride with 1-bromo-3-phenylpropane and subsequent salt formation with methanolic hydrogen chloride as described in Step 3 of Example 1 in 63% overall yield.

$^1$H NMR (CDCl$_3$): δ=12.5 (bs, 1H), 7.42-7.20 (m, 5H), 7.36 (s, 4H), 3.51 (bd, J=7.8 Hz, 2H), 3.09 (m, 2H), 2.99 (m, 4H), 2.78 (t, J=7.2 Hz, 2H), 2.32 (m, 2H) and 2.13 ppm (m, 2H). Mass Spectrum: m/z=332 [M+H]$^+$ Example 4

Preparation of 2-Benzyl-3-[4-(4-chlorophenyl)-4-fluoropiperidin-1-yl]propionic acid Hydrochloride

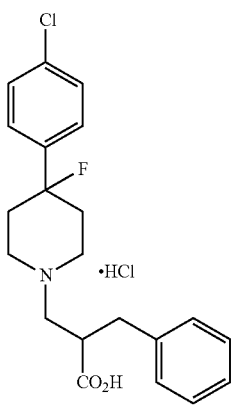 [SMILES: O=C(O)C(Cc1ccccc1)CN1CCC(F)(c2ccc(Cl)cc2)CC1 ; Cl]

Step 1: Preparation of Methyl 3-[4-(4-Chlorophenyl)-4-fluoropiperidin-1-yl]propionate. To a solution of 3-[4-(4-chlorophenyl)-4-fluoropiperidine hydrochloride (280 mg, 1.12 mmol) in methanol (5 mL) was added sodium bicarbonate (500 mg, 5.94 mmol) followed by methyl acrylate (1 mL). The resulting mixture was stirred at room temperature for 14 hours then filtered and concentrated under reduced pressure. The residue was treated with ethyl acetate (10 mL) and the resulting suspension re-filtered and concentrated under reduced pressure. This afforded methyl 3-[4-(4-chlorophenyl)-4-fluoropiperidin-1-yl]propionate as a viscous yellow oil in 94% yield, which was used without further purification.

$^1$H NMR (CDCl$_3$): δ=7.32 (s, 4H), 3.71 (s, 3H), 2.83 (m, 2H), 2.79 (t, J=7.3 Hz, 2H), 2.56 (t, J=7.3 Hz, 2H), 2.47 (bt, J=11.6 Hz, 2H), 2.14 (td, J=13.3, 4.4 Hz, 2H) and 1.98 ppm (m, 2H).

Step 2: Preparation of Methyl 2-Benzyl-3-[4-(4-Chlorophenyl)-4-fluoropiperidin-1-yl]propionate Hydrochloride. A solution of methyl 3-[4-(4-chlorophenyl)-4-fluoropiperidin-1-yl]propionate (75 mg, 0.23 mmol) in toluene (5 mL) was placed under a dry nitrogen atmosphere and cooled in a dry ice acetone bath. A 1M solution of lithium hexamethyldisilazide (0.28 mL, 0.28 mmol) was then added drop-wise over 10 minutes. The resulting bright yellow solution was stirred for 1 hour then benzyl bromide (43 mg, 0.25 mmol) added in one portion. The reaction was then allowed to warm to room temperature with stirring over a 16 hour period then quenched by the addition of 25% aqueous ammonium chloride solution (10 mL). The resulting mixture was extracted with ethyl acetate (2×10 mL) and the combined extracts dried over magnesium sulfate, filtered and stripped to a viscous yellow oil. This oil was treated with 10% methanolic hydrogen chloride (5 mL) and the solution re-concentrated. The resulting oil was triturated with 1:1 ethyl acetate/heptanes (10 mL) to afford a light yellow solid which was collected by filtration. After drying under vacuum for 12 hours methyl 2-benzyl-3-[4-(4-chlorophenyl)-4-fluoropiperidin-1-yl]propionate hydrochloride was obtained as a light yellow solid in 44% yield.

$^1$H NMR (CDCl$_3$): δ=12.25 (bs, 1H), 7.33-7.18 (m, 5H), 7.21 (s, 4H), 3.61 (s, 3H), 3.36 (m, 4H), 3.01 (m, 5H) and 1.96 ppm (m, 4H). Mass Spectrum: m/z=390 [M+H]$^+$ Step 3: Preparation of 2-Benzyl-3-[4-(4-chlorophenyl)-4-fluoropiperidin-1-yl]propionic acid Hydrochloride. To a solution of methyl 2-benzyl-3-[4-(4-chlorophenyl)-4-fluoropiperidin-1-yl]propionate hydrochloride in methanol (2.5 mL) was added 50% aqueous sodium hydroxide solution (1 mL) and the resulting solution heated to reflux under N$_2$ for 14 hours. After this time the reaction was cooled and concentrated. The residue was treated with 2N hydrochloric acid (6 mL) and the mixture stirred for 1 hr. The reaction was then extracted with 2-butanone (3×10 mL) and the extracts dried over magnesium sulfate, filtered and concentrated. The oily residue was re-dissolved in EtOAc (10 mL) re-filtered and concentrated. The residue was then re-dissolved in 2-butanone and concentrated to afford a yellow foam. This material was dried under high vacuum for 16 hours to afford a 55% yield of the title compound as a yellow foam.

$^1$H NMR (CD$_3$OD): δ=7.43 (bs, 4H), 7.39-7.22 (m, 5H), 3.60 (m, 4H), 3.47 (bd, J=10.6 Hz, 1H), 3.04 (dd, J=14.0, 5.8 Hz, 1H) 2.98 (m, 1H) 2.51 (m, 2H) 2.39 (m, 1H) and 2.22 ppm (m, 3H). Mass Spectrum: m/z=376 [M+H]$^+$

Example 5

Preparation of 2,2-Dibenzyl-3-[4-(4-chlorophenyl)-4-fluoropiperidin-1-yl]propionic acid Hydrochloride

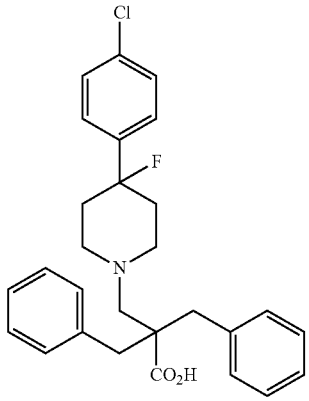 [SMILES: O=C(O)C(Cc1ccccc1)(Cc1ccccc1)CN1CCC(F)(c2ccc(Cl)cc2)CC1]

Step 1: Preparation of Methyl 2,2-Dibenzyl-3-[4-(4-chlorophenyl)-4-fluoropiperidin-1-yl]propionate. This compound was prepared from methyl 3-[4-(4-chlorophenyl)-4-fluoropiperidin-1-yl]propionate and 2.5 equivalents of both lithium hexamethyldisilazide and benzyl bromide as described in Step 2 of Example 4 in 38% yield.

$^1$H NMR (CDCl$_3$): δ=11.26 (bs, 1H), 7.45 (d, J=8.5 Hz, 2H), 7.32 (m, 8H), 7.28 (s, 4H), 3.79 (s, 3H), 3.58 (d, J=5.5 Hz, 4H), 3.49 (m, 2H), 3.21 (m, 3H), 2.17 (m, 2H) and 1.96 ppm (t, J=9.5 Hz, 1H). Mass Spectrum: m/z=480 [M+H]$^+$ Step 2: Preparation of 2,2-Dibenzyl-3-[4-(4-chlorophenyl)-4-fluoropiperidin-1-yl]-propionic acid hydrochloride. The title compound was obtained by the hydrolysis of methyl 2,2-dibenzyl-3-[4-(4-chlorophenyl)-4-fluoropiperidin-1-yl] propionate and subsequent acidification with hydrochloric acid as described in Step 3 of Example 4 in 61% overall yield.

$^1$H NMR (CDCl$_3$): δ=8.92 (bs, 1H), 7.42 (d, J=8.8 Hz, 2H), 7.26 (bs, 12H), 5.48 (bs, 1H), 3.57 (bd, J=14.0 Hz, 2H), 3.46 (m, 1H), 3.18 (m, 1H), 3.04 (bs, 5H) 2.91 (bd, J=14.2 Hz, 2H) and 2.77 ppm (bs, 3H).

Example 6

Preparation of 1-(3,3-diphenylpropyl)-4-fluoro-4-(3-hydroxyphenyl)piperidine Hydrochloride

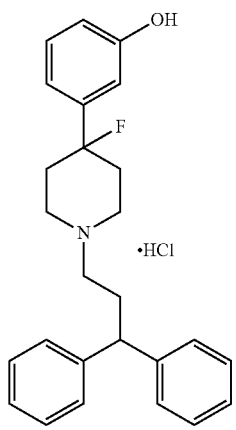 [SMILES: Oc1cccc(C2(F)CCN(CCC(c3ccccc3)c3ccccc3)CC2)c1 ; Cl]

Step 1: Preparation of tert-Butyl 4-(3-Benzyloxyphenyl)-4-hydroxypiperidine-1-carboxylate. A suspension of magnesium metal (0.144 g, 6.0 mmol) in THF (10 mL) was rapidly stirred for 30 minutes under nitrogen then a solution of 3-benzyloxybromobenzene (1.58 g, 6.00 mmol) in THF (10 mL) added slowly via dropping funnel. Once approximately 1 mL of the bromide solution had been added a crystal of iodine was added to the reaction and the mixture gently heated until Grignard formation began. The remaining bromide solution was then added at a rate to maintain a reaction temperature range of 50-60° C. Once addition was complete the reaction was heated to gentle reflux for 1 hour then cooled in an ice bath. A solution of tert-Butyl 4-oxopiperidine-1-carboxylate (1.00 g, 5.02 mmol) in THF (10 mL) was the added to the reaction over a period of 30 minutes then the mixture was allowed to warm to room temperature with stirring over a 2 hour period. After this time the reaction was quenched by the addition of 25% ammonium chloride solution (50 mL) and the layers separated. The aqueous was extracted with ethyl acetate (2×10 mL) and the combined organics were washed with water (20 mL) and brine (20 mL) then dried over magnesium sulfate. Subsequent filtration, concentration and purification of the residue by column chromatography (SiO$_2$, 0-25% ethyl acetate/heptanes) afforded a 61% yield of tert-butyl 4-(3-benzyloxyphenyl)-4-hydroxypiperidine-1-carboxylate as a viscous clear oil that became a white solid on standing.

$^1$H NMR (CDCl$_3$): δ=7.41-7.33 (m, 5H), 7.29 (d, J=7.3 Hz, 1H), 7.15 (t, J=1.9 Hz, 1H), 7.06 (d, J=7.8 Hz, 1H), 6.91 (dd, J=8.0, 2.1 Hz, 1H), 5.09 (s, 2H), 4.03 (m, 2H), 3.25 (bt, J=12 Hz, 2H), 2.00 (bt, J=11.1 Hz, 2H), 1.73 (bd, J=12.6 Hz, 2H) and 1.50 ppm (s, 9H).

Step 2: Preparation of 4-(3-benzyloxyphenyl)-4-fluoropiperidine Hydrochloride. This material was prepared from the reaction of tert-butyl 4-(3-benzyloxyphenyl)-4-hydroxypiperidine-1-carboxylate with diethylaminosulfur trifluoride followed by direct deprotection of the crude product with methanolic hydrogen chloride as described in Step 2 of Example 1 in 75% overall yield.

$^1$H NMR (CDCl$_3$): δ=7.43 (d, J=7.0 Hz, 1H), 7.40-7.16 (m, 6H), 7.14 (d, J=6.7 Hz, 1H), 7.03 (m, 1H), 5.06, (s, 2H), 3.57 (m, 3H), 3.07 (dd, J=14.0, 6.9 Hz, 1H), 2.94 (m, 1H), 2.64 (m, 1H), 2.52 (q, J=11.2 Hz, 1H) and 1.94 ppm (m, 1H).

Step 3: Preparation of 4-(3-Benzyloxyphenyl)-1-(3,3-diphenylpropyl)-4-fluoropiperidine Hydrochloride. This material was obtained by the alkylation of 4-(3-benzyloxyphenyl)-4-fluoropiperidine hydrochloride with 3,3-diphenyl-1-iodopropane and subsequent salt formation with methanolic hydrogen chloride as described in Step 3 of Example 1 in 59% overall yield.

$^1$H NMR (CDCl$_3$): δ=12.52 (bs, 1H), 7.46-7.14 (m, 16H), 7.11 (s, 1H), 7.02 (d, J=8.1 Hz, 1H), 6.93 (dd, J=8.1, 2.2 Hz, 1H), 5.07 (s, 2H), 4.08 (m, 2H), 3.52 (bs, 2H), 3.06 (m, 2H), 2.93 (m, 2H), 2.74 (bs, 2H) and 2.10 ppm (m, 3H).

Step 4: Preparation of 1-(3,3-Diphenylpropyl)-4-fluoro-4-(3-hydroxyphenyl)piperidine Hydrochloride. A solution of 4-(3-benzyloxyphenyl)-1-(3,3-diphenyl-propyl)-4-fluoropiperidine hydrochloride (40 mg, 0.08 mmol) in methanol (5 mL) was treated with palladium on carbon (10 mg, 10% Pd, 50% H$_2$O) and the mixture rapidly stirred under 1 atmosphere of hydrogen gas for 8 hours. After this time the hydrogen was replaced by nitrogen and the reaction mixture filtered through a celite pad. The pad was washed with additional methanol (10 mL) and the filtrate concentrated under reduced pressure. Trituration of the residue with a 1:1 mixture of 2-butanone/ethyl acetate (10 mL) and subsequent filtration and drying afforded a 64% yield of 1-(3,3-diphenylpropyl)-4-fluoro-4-(3-hydroxyphenyl)piperidine hydrochloride as an off-white solid.

¹H NMR (CD₃OD): δ=7.33 (m, 8H), 7.22 (m, 2H), 7.13 (t, J=7.8 Hz, 2H), 6.69 (m, 2H), 4.07 (t, J=7.9 Hz, 1H), 3.63 (bd, J=11.8 Hz, 2H), 3.05 (m, 2H), 2.93 (m, 2H), 2.79 (pent, J=7.4 Hz, 1H) 2.61 (m, 2H) and 2.04 ppm (m, 3H). Mass Spectrum: m/z=373 [M-OH+H]⁺

Example 7

Preparation of 2,2-Dibenzyl-3-[4-fluoro-4-(3-hydroxyphenyl)-piperidin-1-yl]propionic acid Hydrochloride

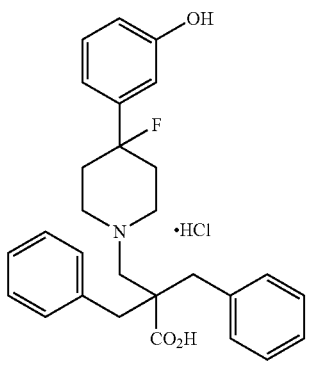 [SMILES: O=C(O)C(Cc1ccccc1)(Cc1ccccc1)CN1CCC(F)(c2cccc(O)c2)CC1 ; Cl]

Step 1: Preparation of Methyl 3-[4-(3-Benzyloxyphenyl)-4-fluoropiperidin-1-yl]propionate. This compound was prepared from 4-(3-benzyloxyphenyl)-4-fluoropiperidine hydrochloride and methyl acrylate as described in Step 1 of Example 4 in 86% yield.

¹H NMR (CDCl₃): δ=7.43-7.23 (m, 6H), 7.05 (t, J=1.9 Hz, 1H), 6.97 (t, J=7.5 Hz, 1H), 6.88 (m, 1H), 5.03 (s, 2H), 3.67 (s, 3H), 2.80 (m, 1H), 2.76 (t, J=3.4 Hz, 2H), 2.70 (t, J=5.6 Hz, 1H), 2.57 (m, 1H), 2.52 (t, J=3.4 Hz, 2H), 2.40 (dd, J=7.9, 2.5 Hz, 1H), 2.12 (ddd, J=26.7, 13.4, 0.5 Hz 1H) and 1.98 ppm (m, 3H).

Step 2: Preparation of Methyl 2,2-Dibenzyl 3-[4-(3-benzyloxyphenyl)-4-fluoropiperidin-1-yl]propionate. This compound was prepared from methyl 3-[4-(3-benzyloxyphenyl)-4-fluoropiperidin-1-yl]propionate and 2.5 equivalents of both lithium hexamethyldisilazide and benzyl bromide as described in Step 2 of Example 4 with the exception that THF was used as the reaction solvent as opposed to toluene. The desired product was obtained in 42% overall yield.

¹H NMR (CDCl₃): δ=7.41-7.11 (m, 14H), 7.06 (t, J=1.8 Hz, 1H), 6.93 (m, 2H), 6.89 (dd, J=8.0, 2.1 Hz, 2H), 5.02 (s, 2H), 3.69 (s, 3H), 3.66-3.52 (m, 4H), 3.45 (bd, J=10.4 Hz, 2H), 3.34 (m, 1H), 3.23-3.09 (m, 3H) 7.06 (td, J=13.8, 7.0 Hz, 2H), and 2.05 ppm (m, 2H). Mass Spectrum: m/z=552 [M+H]⁺

Step 3: Preparation of 2,2-Dibenzyl-3-[4-(3-hydroxyphenyl)-4-fluoropiperidin-1-yl]-propionic acid Hydrochloride. This material was obtained by debenzylation of methyl 2,2-dibenzyl 3-[4-(3-benzyloxyphenyl)-4-fluoropiperidin-1-yl]propionate as described Step 4 of Example 6, followed by immediate alkaline hydrolysis and salt formation as described in Step 3 of Example 4. This afforded the title compound in 33% overall yield.

¹H NMR (CDCl₃): δ=7.33 (bs, 8H), 7.27-7.13 (m, 4H), 6.73 (m, 2H), 5.48 (bs, 1H), 3.73 (bd, J=10.5 Hz, 2H), 3.23 (d, J=13.7 Hz, 2H), 3.13 (d, J=13.7 Hz, 2H), 3.02 (m, 1H) 2.95 (m, 1H), 2.83 (m, 2H) 2.25 (m, 1H) and 2.02 ppm (bs, 3H). Mass Spectrum: m/z=430 [M-OH]

Example 8

Preparation of 1,1-Dibenzyl-3-[4-fluoro-4-(3-hydroxyphenyl)piperidin-1-yl]propan-1-ol Hydrochloride

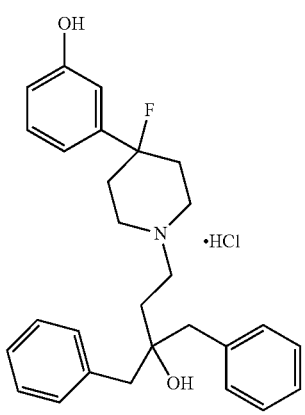 [SMILES: Oc1cccc(C2(F)CCN(CCC(O)(Cc3ccccc3)Cc3ccccc3)CC2)c1 ; Cl]

Step 1: Preparation of 3-[4-(3-Benzyloxyphenyl)-4-fluoropiperidin-1-yl]-1,1-dibenzylpropan-1-ol. A solution of methyl 3-[4-(3-benzyloxyphenyl)-4-fluoropiperidin-1-yl] propionate (100 mg, 0.27 mmol) in THF (5 mL) was cooled in an ice bath and a 2M solution of benzylmagnesium chloride in THF (0.338 mL, 0.68 mmol) added dropwise over 5 minutes. The resulting yellow solution was then stirred for 14 h during which time the reaction reached room temperature. The mixture was then quenched with 25% aqueous ammonium chloride solution (10 mL) and diluted with ethyl acetate (3×10 mL). The organic layers were then combined and dried over magnesium sulfate. Subsequent filtration, concentration and purification by silica gel chromatography (SiO₂, 50% ethyl acetate/heptanes) afforded 3-[4-(3-benzyloxyphenyl)-4-fluoropiperidin-1-yl]-1,1-dibenzylpropan-1-ol as a clear viscous oil in 49% yield.

¹H NMR (CDCl₃): δ=7.33 (bs, 8H), 7.27-7.13 (m, 4H), 6.73 (m, 2H), 5.10 (s, 2H), 2.94 (bd, J=2.6 Hz, 2H), 2.88 (d, J=13.5 Hz, 2H), 2.78 (d, J=13.5 Hz, 2H), 2.57 (t, J=5.8 Hz, 2H) 2.51 (m, 1H), 2.44 (m, 3H), 2.25 (m, 1H), 1.94 (m, 1H) and 1.63 ppm (t, J=5.8 Hz, 2H).

Step 2: Preparation of 1,1-Dibenzyl-3-[4-fluoro-4-(3-hydroxyphenyl)-piperidin-1-yl]propan-1-ol Hydrochloride. The title compound was prepared via the debenzylation of 3-[4-(3-benzyloxyphenyl)-4-fluoropiperidin-1-yl]-1,1-dibenzylpropan-1-ol as described in Step 4 of Example 6, followed by salt formation using methanolic hydrogen chloride in 77% overall yield.

¹H NMR (CD₃OD): δ=7.35-7.16 (m, 10H), 7.13 (t, J=8.2 Hz, 1H), 6.67 (m, 3H), 3.39 (bs, 2H), 3.12 (t, J=7.8 Hz, 2H), 2.91 (d, J=14.0 Hz, 2H), 2.86 (m, 1H), 2.81 (d, J=14.0 Hz, 2H), 2.75 (m, 1H), 2.01 (m, 2H) and 1.84 ppm (m, 4H).

Example 9

Preparation of 4-fluoro-4-(3-Hydroxyphenyl)-1-(2-phenoxyethyl)piperidine Hydrochloride

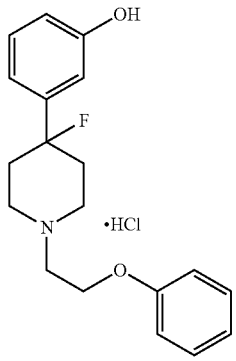 [SMILES: Oc1cccc(C2(F)CCN(CCOc3ccccc3)CC2)c1 ; Cl]

Step 1: Preparation of 4-(3-Benzyloxyphenyl)-4-fluoro)-1-(2-phenoxyethyl)piperidine Hydrochloride. This material was prepared by the alkylation of 4-(3-benzyloxyphenyl)-4-fluoropiperidine hydrochloride with 1-bromo-2-phenoxyethane and subsequent salt formation with 10% methanolic hydrogen chloride as described in Step 3 of Example 1 in 58% overall yield.

$^1$H NMR (CDCl$_3$): δ=13.16 (bs, 1H), 7.48-7.29 (m, 9H), 7.12 (t, J=1.9 Hz, 1H), 7.05 (m, 2H), 6.95 (dd, J=16.1, 8 Hz, 2H), 5.09 (s, 2H), 4.62 (t, J=3.7 Hz, 2H), 3.69 (d, J=10.8 Hz, 2H), 3.52 (bs, 2H), 3.37 (m, 2H), 3.14 (m, 1H), 2.99 (m, 1H) and 2.19 ppm (dd, J=14.4, 9.1 Hz, 2H). Mass Spectrum: m/z=406 [M+H]$^+$ Step 2: Preparation of 4-Fluoro-4-(3-hydroxyphenyl)-1-(2-phenoxyethyl)piperidine Hydrochloride. The title compound was obtained via debenzylation 4-(3-benzyloxyphenyl)-4-fluoro)-1-(2-phenoxyethyl)piperidine hydrochloride as described in Step 4 of Example 6 in 62% yield.

$^1$H NMR (CD$_3$OD): δ=7.34 (t, J=7.5 Hz, 2H), 7.15 (t, J=7.7 Hz, 1H), 7.03 (m, 3H), 6.77-6.66 (m, 3H), 4.42 (bs, 2H), 3.76 (bd, J=10.8 Hz, 2H), 3.52 (bs, 2H), 3.37 (m, 2H), 3.14 (m, 1H), 2.99 (m, 1H) and 2.19 ppm (dd, J=14.4, 9.1 Hz, 2H). Mass Spectrum: m/z=298 [M-OH]$^+$

Example 10

Preparation of 4-fluoro-4-(3-Hydroxyphenyl)-1-(3-phenylpropyl)piperidine Hydrochloride

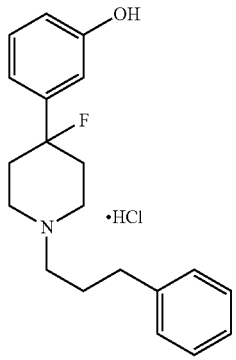 [SMILES: Oc1cccc(C2(F)CCN(CCCc3ccccc3)CC2)c1 ; Cl]

Step 1: Preparation of 4-(3-Benzyloxyphenyl)-4-fluoro-1-(3-phenylpropyl)piperidine Hydrochloride. This material was prepared by the alkylation of 4-(3-benzyloxyphenyl)-4-fluoropiperidine hydrochloride with 1-bromo-3-phenylpropane and subsequent salt formation with methanolic hydrogen chloride as described in Step 3 of Example 1 in 43% overall yield.

$^1$H NMR (CDCl$_3$): δ=12.68 (bs, 1H), 7.48-7.26 (m, 11H), 7.10 (s, 1H), 7.05 (d, J=7.7 Hz, 1H), 6.95 (m, 1H), 5.07 (s, 2H), 3.51 (bd, J=7.2 Hz, 2H), 3.12 (m, 3H), 2.99 (m, 2H) 2.76 (t, J=7.1 Hz, 2H), 2.34 (m, 2H) and 2.13 ppm (m, 2H).

Step 2: Preparation of 4-Fluoro-4-(3-hydroxyphenyl)-1-(3-phenylpropyl)piperidine Hydrochloride. The title compound was obtained via debenzylation 4-(3-benzyloxyphenyl)-4-fluoro)-1-(3-phenylpropyl)piperidine hydrochloride as described in Step 4 of Example 6 in 82% yield.

$^1$H NMR (CDCl$_3$): δ=7.44-7.12 (m, 6H), 6.94 (s, 1H), 6.82 (d, J=7.2 Hz, 1H), 6.73 (d, J=7.4 Hz, 1H), 3.61 (bd, J=8.8 Hz, 2H), 3.24 (m, 2H), 2.95 (m, 2H) 2.76 (t, J=7.0 Hz, 2H), 2.66 (m, 4H) and 2.16 ppm (m, 2H). Mass Spectrum: m/z=296 [M-OH]$^+$

Example 11

Preparation of 1-(3-Cyclohexylpropyl)-4-fluoro-4-(3-hydroxyphenyl)piperidine Hydrochloride

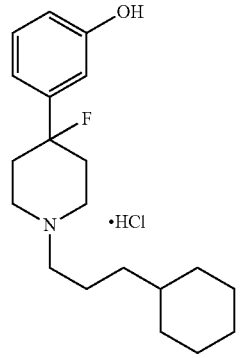 [SMILES: Oc1cccc(C2(F)CCN(CCCC3CCCCC3)CC2)c1 ; Cl]

Step 1: Preparation of 4-(3-Benzyloxyphenyl)-1-(3-cyclohexylpropyl)-4-fluoropiperidine Hydrochloride. This material was prepared by the alkylation of 4-(3-benzyloxyphenyl)-4-fluoropiperidine Hydrochloride with 1-bromo-3-cyclohexylpropane and subsequent salt formation with methanolic hydrogen chloride as described in Step 3 of Example 1 in 32% overall yield.

$^1$H NMR (CDCl$_3$): δ=12.72 (bs, 1H), 7.48-7.26 (m, 6H), 7.12 (t, J=2.0 Hz, 1H), 7.04 (d, J=7.9 Hz, 1H), 6.94 (m, 2H), 5.09 (s, 2H), 3.54 (bd, J=7.3 Hz, 2H), 3.16 (m, 3H), 2.98 (bs, 2H), 2.15 (m, 2H), 1.98 (bs, 2H), 1.72 (m, 6H), 1.23 (m, 6H) and 0.91 ppm (m, 2H).

Step 2: Preparation of 1-(3-Cyclohexylpropyl)-4-fluoro-4-(3-hydroxyphenyl)piperidine Hydrochloride. The title compound was obtained via debenzylation 4-(3-benzyloxy-phenyl)-1-(3-cyclohexylpropyl)-4-fluoropiperidine Hydrochloride as described in Step 4 of Example 6 in 69% yield.

$^1$H NMR (CD$_3$OD): δ=7.15 (t, J=7.8 Hz, 1H), 6.74 (d, J=7.8 Hz, 1H), 6.71 (s, 1H), 6.68 (d, J=7.8 Hz, 1H), 3.66 (bd, J=11.7 Hz, 2H), 3.11 (m, 4H), 2.83 (m, 1H), 2.13 (m, 2H), 2.02 (m, 2H), 1.78 (m, 6H), 1.27 (m, 6H) and 0.99 ppm (m, 2H). Mass Spectrum: m/z=302 [M-OH]$^+$

Example 12

Preparation of 4-fluoro-4-(3-hydroxyphenyl)-1-(3-phenylpropyl)-3-methylpiperidine Hydrochloride

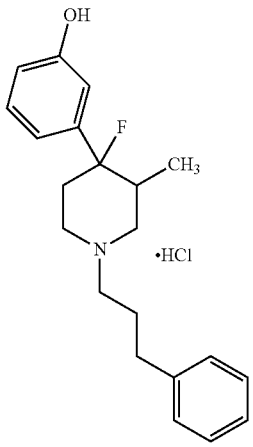 [SMILES: CC1CN(CCCc2ccccc2)CCC1(F)c1cccc(O)c1 ; Cl]

Step 1: Preparation of tert-Butyl 4-(3-benzyloxyphenyl)-4-hydroxy-3-methylpiperidine-1-carboxylate. This compound was prepared from tert-Butyl 3-methyl-4-oxopiperidine-1-carboxylate and 3-benzyloxyphenylmagnesium bromide as described in Step 1 of Example 6 in 44% yield.

$^1$H NMR (CDCl$_3$): δ=7.40-7.35 (m, 5H), 7.23 (t, J=7.0 Hz, 1H), 7.12 (bs, 1H), 7.06 (d, J=8.0 Hz, 1H), 6.91 (d, J=8.0 Hz, 1H), 5.03 (s, 2H), 3.98 (m, 2H), 3.17 (bs, 1H), 2.98 (bs, 1H), 2.05 (m, 1H), 1.90 (m, 1H), 1.66 (bd, J=11.7 Hz, 2H), 1.47 (s, 9H) and 0.60 ppm (d, J=6.6 Hz, 3H).

Step 2: Preparation of 4-(3-benzyloxyphenyl)-4-fluoro-3-methylpiperidine Hydrochloride. This material was prepared from the reaction of tert-Butyl 4-(3-benzyloxyphenyl)-4-hydroxy-3-methylpiperidine-1-carboxylate with diethylaminosulfur trifluoride and deprotection of the crude product using methanolic hydrogen chloride as described in Step 2 of Example 1. This afforded 4-(3-benzyloxyphenyl)-4-fluoro-3-methylpiperidine Hydrochloride in 72% overall yield.

$^1$H NMR (CD$_3$OD): δ=9.90 (bs, 1H), 9.70 (bs, 1H), 7.42 (bs, 6H), 7.03-6.91 (m, 3H), 5.06, (s, 2H), 3.47 (m, 1H), 3.04 (m, 3H), 2.70 (m, 2H), 2.07 (m, 1H) and 0.72 ppm (bs, 3H).

Step 3: Preparation of 4-(3-benzyloxyphenyl)-4-fluoro-3-methyl-1-(3-phenylpropyl)piperidine Hydrochloride. This material was obtained by the alkylation of 4-(3-benzyloxyphenyl)-4-fluoro-3-methylpiperidine hydrochloride with 3-phenyl-1-bromopropane and subsequent salt formation with methanolic hydrogen chloride as described in Step 3 of Example 1 in 32% overall yield.

$^1$H NMR (CD$_3$OD): δ=7.44 (d, J=7.2 Hz, 1H), 7.38 (d, J=6.8 Hz, 1H), 7.35-7.22 (m, 6H), 7.01 (m, 3H), 5.12 (s, 2H), 3.55 (m, 2H), 3.22 (bs, 3H), 3.06 (bt, J=12.3 Hz, 1H), 2.75 (bs, 2H), 2.62 (m, 1H), 2.48 (m, 1H), 2.17 (m, 3H) and 0.73 ppm (d, J=6.7 Hz, 3H).

Step 4: Preparation of 4-fluoro-4-(3-hydroxyphenyl)-1-(3-phenylpropyl)-3-methylpiperidine Hydrochloride. The title compound was prepared by the debenzylation of 4-(3-benzyloxyphenyl)-4-fluoro-3-methyl-1-(3-phenylpropyl)piperidine hydrochloride as described in Step 4 of Example 6 in 88% yield.

$^1$H NMR (CDCl$_3$): δ=7.33-7.16 (m, 6H), 6.94 (m, 2H), 6.83 (m, 1H), 3.68 (t, J=6.4 Hz, 1H), 3.40 (bs, 2H), 3.25 (m, 1H) 3.06 (m, 2H), 2.85-2.68 (m, 4H) 2.26 (bs, 2H), 1.89 (m, 1H) and 0.62 ppm (d, J=6.8 Hz, 3H). Mass Spectrum: m/z=328 [M+H]$^+$

Example 13

Preparation of 4-fluoro-4-(3-Hydroxyphenyl)-3-methyl-1-(2-phenoxyethyl)piperidine Hydrochloride

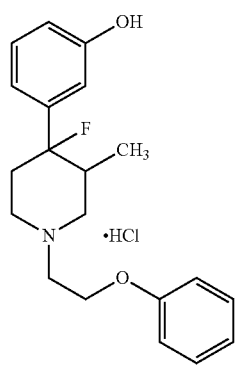 [SMILES: CC1CN(CCOc2ccccc2)CCC1(F)c1cccc(O)c1 ; Cl]

Step 1: Preparation of 4-(3-benzyloxyphenyl)-4-fluoro-3-methyl-1-(2-phenoxyethyl)piperidine Hydrochloride. This material was prepared by the alkylation of 4-(3-benzyloxyphenyl)-4-fluoro-3-methylpiperidine hydrochloride with 1-bromo-2-phenoxyethane and subsequent salt formation with methanolic hydrogen chloride as described in Step 3 of Example 1 in 67% overall yield.

$^1$H NMR (CD$_3$OD): δ=7.47-7.29 (m, 8H), 7.03 (m, 6H), 5.12 (s, 2H), 4.47 (t, J=2.5 Hz, 2H), 3.72 (bs, 2H), 3.63-3.36 (m, 2H), 2.60 (m, 2H) 2.25 (m, 1H) and 0.77 ppm (d, J=6.8 Hz, 3H).

Step 2: Preparation of 4-Fluoro-4-(3-hydroxyphenyl)-3-methyl-1-(2-phenoxyethyl)piperidine Hydrochloride. The title compound was obtained via debenzylation of 4-(3-benzyloxyphenyl)-4-fluoro-3-methyl-1-(2-phenoxyethyl)piperidine hydrochloride as described in Step 4 of Example 6 in 91% yield.

$^1$H NMR (CDCl$_3$): δ=7.20 (m, 2H), 7.08 (t, J=7.7 Hz, 1H), 6.96 (m, 2H), 6.83 (m, 3H), 4.47 (bs, 2H), 3.47 (m, 4H), 3.17 (bs, 1H), 2.89 (m, 2H), 2.28 (bs, 1H), 2.09 (d, J=8.6 Hz, 1H) and 0.61 ppm (d, J=4.6 Hz, 3H). Mass Spectrum: m/z=330 [M+H]$^+$

Example 14

Preparation of 1-(3-cyclohexylpropyl)-4-fluoro-4-(3-hydroxyphenyl)-3-methyl piperidine Hydrochloride

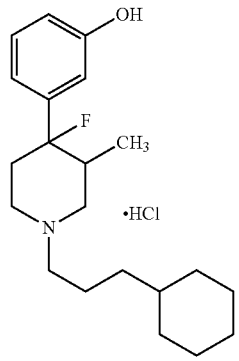 [SMILES: CC1CN(CCCC2CCCCC2)CCC1(F)c1cccc(O)c1 ; Cl]

Step 1: Preparation of 4-(3-benzyloxyphenyl)-1-(3-cyclohexylpropyl)-4-fluoro-3-methylpiperidine Hydrochloride. This material was prepared by the alkylation of 4-(3-benzyloxyphenyl)-4-fluoro-3-methylpiperidine hydrochloride with 1-bromo-3-cyclohexylpropane and subsequent salt formation with methanolic hydrogen chloride as described in Step 3 of Example 1 in 48% overall yield.

$^1$H NMR (CD$_3$OD): δ=7.46-7.31 (m, 6H), 6.99 (m, 3H), 5.12 (s, 2H), 3.57 (m, 2H), 3.12 (m, 5H), 2.60 (m, 1H), 2.46 (m, 1H), 2.20 (m, 1H), 1.72 (m, 6H), 1.23 (m, 6H), 0.91 ppm (m, 2H) and 0.76 ppm (d, J=6.7 Hz, 3H).

Step 2: Preparation of 1-(3-Cyclohexylpropyl)-4-fluoro-4-(3-hydroxyphenyl)-3-methylpiperidine Hydrochloride. The title compound was obtained via debenzylation of 4-(3-benzyloxyphenyl)-1-(3-cyclohexylpropyl)-4-fluoro-3-methylpiperidine hydrochloride as described in Step 4 of Example 6 in 54% yield.

$^1$H NMR (CDCl$_3$): δ=6.89 (m, 2H), 6.75 (d, J=6.9 Hz, 1H), 6.64 (m, 1H), 3.54 (bs, 1H), 3.42 (m, 1H), 2.98 (m, 3H), 2.79 (m, 1H), 1.83 (m, 2H), 1.60 (m, 5H), 1.17 (m, 6H) 0.81 ppm (m, 2H) and 0.69 ppm (d, J=6.5 Hz, 3H). Mass Spectrum: m/z=334 [M+H]$^+$ yphenyl)-4-fluoro-3-methylpiperidin-1-yl]propionate and 2.5 equivalents of both lithium hexamethyldisilazide and benzyl bromide as described in Step 2 of Example 4 with the exception that THF was used as the reaction solvent as opposed to toluene. The desired compound was obtained in 42% overall yield.

$^1$H NMR (CD$_3$OD): δ=7.45 (m, 5H), 7.38-7.27 (m, 11H), 7.04 (m, 1H), 6.95 (m, 2H), 5.09 (s, 2H), 3.73 (s, 3H), 3.71 (m, 4H), 3.69-3.49 (m, 3H), 3.05 (m, 4H), 2.52 (m, 1H), 2.21 (m, 1H) and 0.69 ppm (t, J=6.7 Hz, 3H). Mass Spectrum: m/z=566 [M+H]$^+$ Step 3: Preparation of 2,2-Dibenzyl-3-[4-(3-hydroxyphenyl)-4-fluoro-3-methylpiperidin-1-yl]propionic acid Hydrochloride. The title compound was obtained by the debenzylation of methyl 3-[4-(3-benzoxyphenyl)-4-fluoropiperidin-1-yl]-2,2-dibenzylpropionate as described Step 4 of Example 6, followed by immediate alkaline hydrolysis and salt formation as described in Step 3 of Example 4. This afforded the title compound in 38% overall yield.

$^1$H NMR (DMSO-d$_6$):=7.29 (m, 10H), 7.12 (t, J=7.7 Hz, 1H), 6.79 (bs, 2H), 6.71 (m, 1H), 3.22 (m, 4H), 3.13 (d, J=15.1 Hz, 2H), 2.98 (m, 3H), 2.84 (m, 1H), 2.76 (bs, 1H) and 0.56 ppm (t, J=5.4 Hz, 3H). Mass Spectrum: m/z=462 [M+H]$^+$ Example 15

Preparation of 2,2-Dibenzyl 3-[4-(3-hydroxyphenyl)-4-fluoro-3-methylpiperidin-1-yl]propionic Acid Hydrochloride Example 16

Preparation 4-(3-Aminophenyl)-1-(2-phenoxyethyl) 4-fluoropiperidine Dihydrochloride

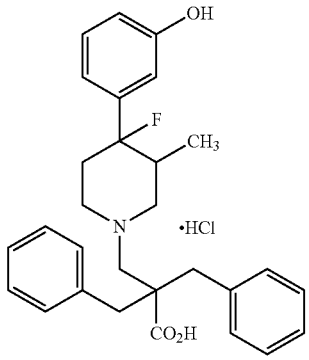 [SMILES: CC1CN(CC(Cc2ccccc2)(Cc2ccccc2)C(=O)O)CCC1(F)c1cccc(O)c1 ; Cl]

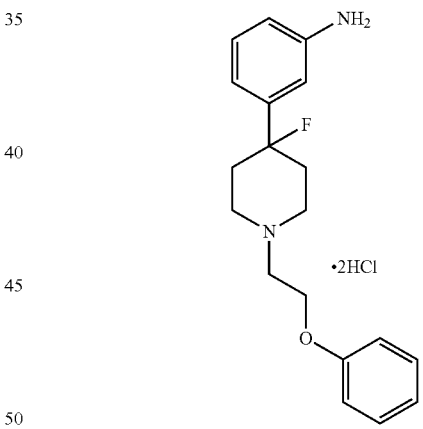

Step 1: Preparation of Methyl 3-[4-(3-Benzyloxyphenyl)-4-fluoro-3-methylpiperidin-1-yl]propionate. This compound was prepared from 4-(3-benzyloxyphenyl)-4-fluoro-3-methylpiperidine hydrochloride and methyl acrylate as described in Step 1 of Example 4 in 81% yield.

$^1$H NMR (CDCl$_3$): δ=7.44-7.29 (m, 5H), 7.25 (t, J=8.0 Hz, 1H), 6.99 (t, J=1.8 Hz, 1H), 6.88 (m, 2H), 5.04 (s, 2H), 3.69 (s, 3H), 2.75 (m, 4H), 2.56 (t, J=7.3 Hz, 2H), 2.41 (m, 1H), 2.20 (m, 2H), 2.11 (m, 1H), 1.99 (dt, J=11.7, 3.1 Hz, 1H) and 0.66 ppm (d, J=6.3 Hz, 3H).

Step 2: Preparation of Methyl 3-[4-(3-Benzyloxyphenyl)-4-fluoro-3-methylpiperidin-1-yl]-2,2-dibenzylpropionate. This compound was prepared from methyl 3-[4-(3-benzylox- Step 1: Preparation of tert-Butyl 4-(3-N,N-dibenzylaminophenyl)-4-hydroxypiperidine-1-carboxylate. A suspension of magnesium metal (0.192 g, 8.00 mmol) in THF (20 mL) was rapidly stirred for 30 minutes under nitrogen then a solution of 3-dibenzylamino-bromobenzene (2.50 g, 7.09 mmol) in THF (10 mL) added slowly via dropping funnel. Once approximately 2 mL of the solution had been added a crystal of iodine was added to the reaction and the mixture gently heated until Grignard formation began. The remaining bromide solution was then added at a rate to maintain a reaction temperature range of 40-60° C. Once addition was complete the reaction was heated to gentle reflux for 1 hour then cooled in an ice bath. tert-Butyl 4-oxopiperidine-1-carboxylate (1.30 g, 6.50 mmol) was then added in small portions over a period of 30 minutes. Once this addition was complete the mixture was stirred at 0° C. for one hour. After this time the cooling bath was removed and the reaction stirred at room temperature for an additional 13 hours. The reaction was then quenched by the addition of 25% ammonium chloride solution (50 mL) and the organic layer separated. The aqueous was extracted with ethyl acetate (20 mL) and the combined extracts dried over magnesium sulfate and filtered. Subsequent concentration afforded a viscous oil that was purified by column chromatography (20-60% EtOAc/heptanes, silica gel) to afford 1.76 g, (57% yield) of tert-butyl 4-(3-N,N-dibenzylaminophenyl)-4-hydroxypiperidine-1-carboxylate as a viscous clear oil.

$^1$H NMR (CDCl$_3$): δ=7.28-7.12 (m, 8H), 7.09 (t, J=8.0 Hz, 2H), 6.85 (bs, 1H), 6.72 (d, J=7.8 Hz, 1H), 6.58 (dd, J=8.1, 2.2 Hz, 2H), 4.59 (s, 4H), 4.03 (bd, J=5.5 Hz, 2H), 3.47 (bs, 2H), 1.76 (m, 2H), 1.63 (m, 2H) and 1.45 ppm (s, 9H).

Step 2: Preparation of 4-(3-N,N-Dibenzylaminophenyl)-4-fluoropiperidine Dihydrochloride: This material was prepared from tert-butyl 4-(3-N,N-dibenzylaminophenyl)-4-hydroxypiperidine-1-carboxylate via diethylaminosulfur trifluoride mediated fluorination as described in Step 2 of Example 1 with the exception that the reaction was carried out in toluene for solubility purposes. The crude product was deprotected using methanolic hydrogen chloride as described in Step 2 of Example 1 to afford the desired product in 79% overall yield as a white solid.

$^1$H NMR (CD$_3$OD+CDCl$_3$): δ=7.38 (bs, 6H), 7.22-7.11 (m, 8H), 4.83, (s, 4H), 3.32 (m, 4H), 2.59-2.35 (m, 2H) and 1.93 ppm (bs, 2H).

Step 3: Preparation of 4-(3-N,N-Dibenzylaminophenyl)-4-fluoro-1-(2-phenoxyethyl)piperidine Dihydrochloride This material was obtained by the alkylation of 4-(3-N,N-Dibenzylaminophenyl)-4-fluoropiperidine dihydrochloride with 2-phenoxy-1-bromoethane and subsequent salt formation with methanolic hydrogen chloride as described in Step 3 of Example 1 in 72% overall yield.

$^1$H NMR (CD$_3$OD): δ=7.49-7.24 (m, 16H), 7.08-7.01 (m, 3H), 5.01 (s, 4H), 4.47 (t, J=3.7 Hz, 2H), 3.63 (m, 4H), 3.50 (td, J=12.8, 2.21 Hz, 2H), 2.60 (td, J=14.5, 4.6 Hz, 1H) 2.47 (m, 1H) and 2.12 ppm (m, 2H).

Step 4: Preparation 4-(3-Aminophenyl)-1-(2-phenoxyethyl) 4-fluoropiperidine Dihydrochloride: A solution of 4-(3-N,N-Dibenzylaminophenyl)-4-fluoro-1-(2-phenoxyethyl)piperidine Dihydrochloride (500 mg, 0.88 mmol) in methanol (30 mL) was treated with Palladium on carbon (100 mg, 10% Pd, 50% wet) and the mixture rapidly stirred under 1 atmosphere of hydrogen gas for 8 hours. After this time the hydrogen was replaced by nitrogen and the reaction mixture filtered through a celite pad. The pad was washed with additional methanol (10 mL) and the filtrate concentrated under reduced pressure. The resulting viscous tan oil was dried under high vacuum for 28 hours to afford a 70% yield of 4-(3-aminophenyl)-1-(2-phenoxyethyl) 4-fluoropiperidine dihydrochloride as a tan colored glassy solid.

$^1$H NMR (CD$_3$OD): δ=7.55-7.29 (m, 6H), 7.07-7.00 (m, 3H), 4.46 (bs, 2H), 3.83 (bd, J=11.5 Hz, 2H), 3.67 (bs, 2H), 3.04 (m, 1H) and 2.17 ppm (bs, 5H). Mass Spectrum: m/z=297 [M-NH$_3$]$^+$ Example 17

Preparation of N-{3-[4-Fluoro-1-(2-phenoxyethyl) piperidin-4-yl]phenyl}-4-methyl-benzenesulfonamide Hydrochloride

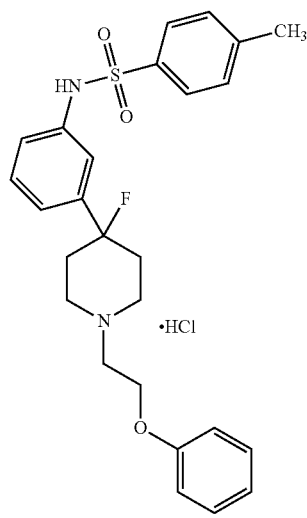 [SMILES: Cc1ccc(S(=O)(=O)Nc2cccc(C3(F)CCN(CCOc4ccccc4)CC3)c2)cc1 ; Cl]

To a suspension of 4-(3-aminophenyl)-1-(2-phenoxyethyl) 4-fluoropiperidine dihydrochloride (100 mg, 0.26 mmol) in methylene chloride (5 mL) was added diisopropylethylamine (118 mg, 0.91 mmol) and the mixture stirred at room temperature until a clear solution resulted. This solution was then cooled to 0° C. and 4-methyl-benzenesulfonyl chloride (58 mg, 0.28 mmol) was then added and the reaction stirred at 0° C. for 1 hour then room temperature for 3 hours. After this time the mixture was quenched by the addition of 25% ammonium chloride solution (10 mL). The organic layer was separated and the aqueous extracted with ethyl acetate (2×10 mL). The combined extracts were dried over magnesium sulfate and filtered and concentrated. The residue was re-dissolved in ethyl acetate (20 mL), washed with water (2×10 mL) and brine (10 mL), dried over magnesium sulfate and filtered. The filtrate was concentrated to a viscous yellow oil which was treated with 10% methanolic hydrogen chloride (10 mL) and re-concentrated. The residue was triturated with ethyl acetate (5 mL) and then dried under high vacuum to afford a 49% yield of the title compound as a light yellow solid.

$^1$H NMR (CDCl$_3$): δ=12.47 (bs, 1H), 12.19 (bs, 1H), 7.76 (t, J=8.6 Hz, 2H), 7.32 (d, J=8.0 Hz, 2H), 7.22 (m, 5H), 7.13 (d, J=6.9 Hz, 1H), 7.02 (t, J=7.3 Hz, 1H), 6.91 (d, J=8.0 Hz, 2H), 4.58 (bs, 2H), 3.83 (bd, J=10.0 Hz, 1H), 3.74 (bd, J=12.6 Hz, 1H), 3.57 (bs, 2H), 3.33 (bd, J=9.1 Hz, 1H), 3.00 (m, 1H), 2.46 (bd, J=8.3 Hz, 1H), 2.36 (s, 3H), 2.10 (dd, J=13.3, 8.3 Hz, 1H), and 1.93 ppm (bs, 2H). Mass Spectrum: m/z=469 [M+H]$^+$

Example 18

Preparation N-{3-[4-Fluoro-1-(2-phenoxyethyl)piperidin-4-yl]phenyl}methane-sulfonamide Hydrochloride

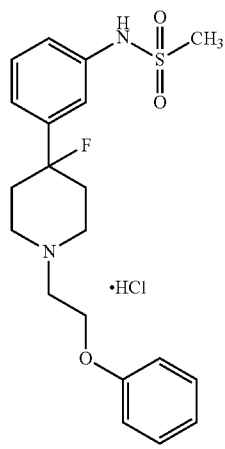 [SMILES: CS(=O)(=O)Nc1cccc(C2(F)CCN(CCOc3ccccc3)CC2)c1 ; Cl]

The title compound was prepared from the reaction of 4-(3-aminophenyl)-1-(2-phenoxyethyl) 4-fluoropiperidine dihydrochloride with methanesulfonyl chloride in the presence of excess diisopropylethylamine as described in Example 17. The desired material was obtained in 64% yield as an off-white solid.

$^1$H NMR (CDCl$_3$): δ=11.83 (bs, 1H), 11.42 (bs, 1H), 7.76 (bs, 1H), 7.30-7.19 (m, 4H), 7.12 (q, J=6.9 Hz, 1H), 6.98-6.90 (m, 3H), 4.48 (bs, 2H), 3.69 (bs, 3H), 3.49 (s, 3H), 3.36 (bd, J=8.9 Hz, 1H), 3.13 (bs, 1H), 2.95-2.70 (m, 2H), 2.29 (m, 1H) and 1.92 ppm (m, 2H). Mass Spectrum: m/z=393 [M+H]$^+$

Example 19

Preparation of 1-tert-Butyl-3-{3-[4-fluoro-1-(2-phenoxyethyl)-piperidin-4-yl]phenyl}-urea

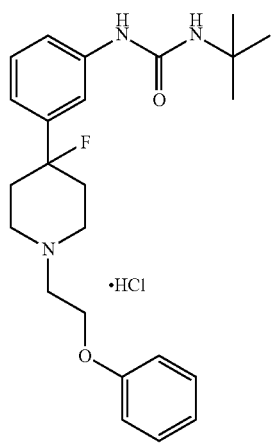 [SMILES: CC(C)(C)NC(=O)Nc1cccc(C2(F)CCN(CCOc3ccccc3)CC2)c1 ; Cl]

The title compound was prepared from the reaction of 4-(3-aminophenyl)-1-(2-phenoxyethyl) 4-fluoropiperidine dihydrochloride with tert-butylisocyanate in the presence of excess diisopropylethylamine as described in Example 19, with the exception that hydrochloride salt formation was not carried out. The desired material was obtained in 24% yield as a white solid.

$^1$H NMR (CDCl$_3$): δ=7.24-7.08 (m, 6H), 6.90-6.77 (m, 3H), 5.26 (bs, 1H), 4.07 (t, J=5.8 Hz, 2H), 3.05 (bd, J=9.5 Hz, 2H), 2.79 (bs, 2H), 2.42 (m, 1H), 2.15 ppm (bs, 2H), 1.75 (bs, 3H) and 1.29 ppm (s, 9H). Mass Spectrum: m/z=414 [M+H]$^+$

Example 20

Preparation of 3-[4-Fluoro-4-(3-hydroxyphenyl)piperidin-1-yl]-N-phenyl-propionamide Hydrochloride

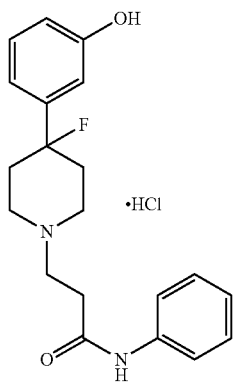 [SMILES: O=C(CCN1CCC(F)(c2cccc(O)c2)CC1)Nc1ccccc1 ; Cl]

Step 1: Preparation of 3-[4-(3-Benzyloxyphenyl)-4-fluoropiperidin-1-yl]-N-(4-bromophenyl)propionamide Hydrochloride. To a solution of N-(4-bromophenyl)acrylamide (340 mg, 1.50 mmol) in methanol (10 mL) was added 4-(3-benzyloxyphenyl)-4-fluoropiperidine hydrochloride (321 mg, 1.00 mmol) followed by sodium bicarbonate (840 mg, 10.0 mmol) and the resulting suspension stirred at room temperature for 52 hours. After this time the reaction was filtered and the filtrate concentrated under reduced pressure. The residue was treated with ethyl acetate (10 mL) and the resulting suspension re-filtered and concentrated under reduced pressure. The resulting solid was treated with 10% hydrogen chloride in methanol (10 mL) and the solution re-concentrated. Subsequent trituration with ethyl acetate (10 mL) afforded 3-[4-(3-benzyloxyphenyl)-4-fluoropiperidin-1-yl]-N-(4-bromophenyl)propionamide hydrochloride in 64% yield as a light yellow solid.

$^1$H NMR (CDCl$_3$): δ=7.36-7.16 (m, 12H), 6.97 (dd=5.9, 1.6 Hz, 2H), 6.85 (m, 2H), 4.99 (s, 2H), 3.21 (d, J=2.7 Hz, 1H), 2.93 (bd, J=11.6 Hz, 1H), 2.74 (m, 3H), 2.54 (m, 1H), 2.49 (bs, 3H) and 2.02 ppm (m, 3H).

Step 2: Preparation of 3-[4-Fluoro-4-(3-hydroxyphenyl)-piperidin-1-yl]-N-phenyl-propionamide Hydrochloride. The title compound was prepared via debenzylation of 3-[4-(3-benzyloxyphenyl)-4-fluoropiperidin-1-yl]-N-(4-bromophenyl)propionamide as described in Step 4 of Example 6 in 73% yield.

$^1$H NMR (CD$_3$OD): δ=7.61 (dd, J=8.6, 1.2 Hz, 2H), 7.33 (m, 2H), 7.14 (m, 2H), 6.89 (bs, 1H), 6.80 (m, 1H), 6.70 (m, 1H), 3.74 (m, 2H), 3.62 (t, J=6.9 Hz, 1H), 3.55 (t, J=6.9 Hz, 1H), 3.46 (m, 1H), 3.20 (m, 1H), 3.09 (m, 1H), 3.00 (t, J=6.8 Hz, 1H), 2.63-2.39 (m, 1H) 2.31 (bd, J=9.1 Hz, 1H) and 2.02 ppm (bt, J=15.2 Hz, 2H). Mass Spectrum: m/z=343 [M+H]$^+$ Example 21

Preparation of 3-[4-Fluoro-4-(3-hydroxyphenyl)-3-methylpiperidin-1-yl]-N-phenylpropionamide Hydrochloride

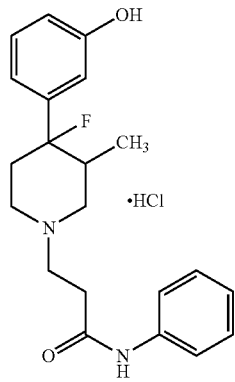 [SMILES: CC1CN(CCC(=O)Nc2ccccc2)CCC1(F)c1cccc(O)c1 ; Cl]

Step 1: Preparation of 3-[4-(3-Benzyloxyphenyl)-4-fluoro-3-methylpiperidin-1-yl]-N-(4-bromophenyl)propionamide Hydrochloride. This material was synthesized by the reaction of N-(4-bromophenyl)acrylamide with 4-(3-benzyloxyphenyl)-4-fluoro-3-methylpiperidine hydrochloride as described in Step 1 of Example 20. The desired compound was obtained as a light yellow solid in 65% yield.

$^1$H NMR (CD$_3$OD): δ=7.59 (d, J=8.6 Hz, 2H), 7.46 (m, 4H), 7.35 (m, 4H), 7.07 (bs, 1H), 7.03 (d, J=8.3 Hz, 1H), 6.96 (m, 1H), 5.13 (s, 2H), 3.61 (m, 5H), 3.05 (m, 4H), 2.61 (m, 1H), 2.28 (bd, J=14.4 Hz, 1H), and 0.77 ppm (d, J=6.8 Hz, 3H).

Step 2: Preparation of 3-[4-Fluoro-4-(3-hydroxyphenyl)-3 methylpiperidin-1-yl]-N-phenylpropionamide Hydrochloride. The title compound was prepared via debenzylation of 3-[4-(3-benzyloxyphenyl)-4-fluoro-3-methylpiperidin-1-yl]-N-(4-bromophenyl)propionamide as described in Step 4 of Example 6 in 88% overall yield.

$^1$H NMR (CD$_3$OD): δ=7.60 (d, J=7.8 Hz, 2H), 7.33 (t, J=7.7 Hz, 2H), 7.25 (m, 1H), 7.12 (t, J=7.4 Hz, 1H), 6.85 (m, 3H), 3.56 (bt, J=6.1 Hz, 2H), 3.49 (bs, 3H), 3.01 (m, 4H), 2.44 (m, 1H), 2.23 (m, 1H) and 0.78 ppm (d, J=7.5 Hz, 3H). Mass Spectrum: m/z=357 [M+H]$^+$ Example 22

Preparation of 1-(3-Cyclohexylpropyl)-4-fluoro-4-(3-methoxyphenyl)piperidine Hydrochloride

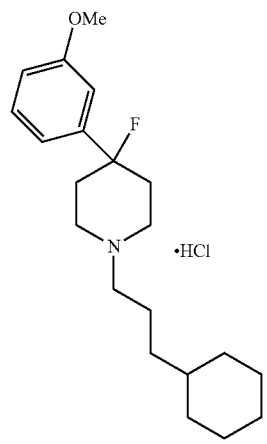 [SMILES: COc1cccc(C2(F)CCN(CCCC3CCCCC3)CC2)c1 ; Cl]

Step 1: Preparation of tert-Butyl 4-hydroxy-4-(3-methoxyphenyl)piperidine-1-carboxylate. This compound was prepared from tert-Butyl 4-oxopiperidine-1-carboxylate and 3-methoxyphenylmagnesium bromide as described in Step 1 of Example 6 in 55% yield.

$^1$H NMR (CDCl$_3$): δ=7.19 (t, J=7.9 Hz, 1H), 7.00 (m, 1H), 6.97 (d, J=7.8 Hz, 1H), 6.72 (dd, J=8.0, 2.0 Hz, 1H), 3.91 (bd, J=12.6 Hz, 2H), 3.72 (s, 3H), 3.17 (bt, J=12.2 Hz, 2H), 3.01 (bs, 1H), 1.87 (dt, J=13.0, 4.6 Hz, 2H), 1.64 (bd, J=12.8 Hz, 2H) and 1.41 ppm (s, 9H).

Step 2: Preparation of 4-(3-Methoxyphenyl)-4-fluoropiperidine hydrochloride. This material was prepared from the reaction of tert-Butyl 4-hydroxy-4-(3-methoxyphenyl)piperidine-1-carboxylate with diethylaminosulfur trifluoride and deprotection of the crude product using methanolic hydrogen chloride as described in Step 2 of Example 1 to afford 4-(3-methoxyphenyl)-4-fluoropiperidine hydrochloride in 76% yield.

$^1$H NMR (CD$_3$OD): δ=7.30 (t, J=8.0 Hz, 1H), 7.00 (m, 2H), 6.67 (td, J=8.2, 1.8 Hz, 1H), 3.82 (s, 3H), 3.68 (bs, 2H), 3.48 (m, 2H), 2.82 (m, 1H), 2.63 (bd, J=15.0 Hz, 1H) 2.41 (bs, 1H), and 2.28 ppm (m, 1H).

Step 3: Preparation of 1-(3-Cyclohexylpropyl)-4-fluoro-4-(3-methoxyphenyl)piperidine Hydrochloride This material was obtained by alkylation of 4-(3-methoxyphenyl)-4-fluoropiperidine hydrochloride with 3-cyclohexyl-1-bromopropane followed by salt formation with methanolic hydrogen chloride as described in Step 3 of Example 1 in 81% overall yield.

$^1$H NMR (CD$_3$OD): δ=7.35 (t, J=8.1 Hz, 1H), 7.01 (m, 2H), 6.68 (dt, J=8.2, 1.7 Hz, 1H), 3.83 (s, 3H), 3.66 (bd, J=9.2 Hz, 2H), 3.36 (m, 2H), 3.20 (t, J=8.4 Hz, 2H), 2.56 (m, 2H), 2.28 (m, 2H), 1.83 (m, 7H), 1.28 (m, 6H) and 0.97 ppm (m, 2H). Mass Spectrum: m/z=334 [M+H]$^+$

Example 23

Preparation of 4-Fluoro-4-(3-methoxyphenyl)-1-(2-thiophen-3-ylethyl)piperidine Hydrochloride

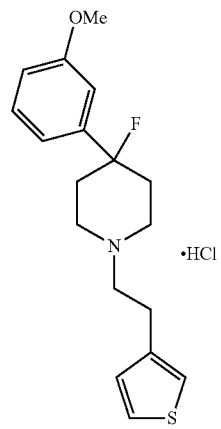 [SMILES: COc1cccc(C2(F)CCN(CCc3ccsc3)CC2)c1 ; Cl]

This material was obtained by the alkylation of 4-fluoro-4-(3-methoxyphenyl)piperidine hydrochloride with 3-(2-bromoethyl)thiophene and subsequent salt formation with methanolic hydrogen chloride as described in Step 3 of Example 1 in 49% overall yield.

$^1$H NMR (CD$_3$OD): δ=7.46 (dd, J=4.9, 2.9 Hz, 1H), 7.36 (t, J=8.2 Hz, 1H), 7.32 (bd, J=1.9 Hz, 1H), 7.12 (dd, J=4.9, 1.1 Hz, 1H), 7.01 (m, 2H), 7.12 (dd, J=8.2, 2.3 Hz, 1H), 3.83 (s, 3H), 3.72 (bd, J=7.9 Hz, 2H), 3.49 (m, 4H), 3.23 (m, 2H), 2.59 (m, 1H), 2.52 (m, 1H) and 2.17 ppm (m, 2H). Mass Spectrum: m/z=320 [M+H]$^+$

Example 24

Preparation of 4-Fluoro-4-(3-hydroxyphenyl)-1-(trans-3-phenylcyclopropylmethyl)-piperidine Hydrochloride

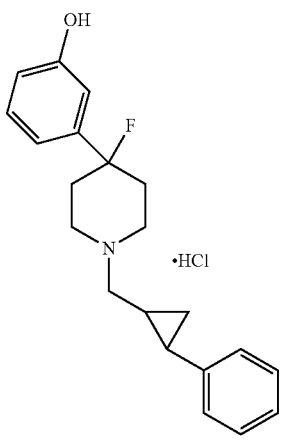 [SMILES: Oc1cccc(C2(F)CCN(CC3CC3c3ccccc3)CC2)c1 ; Cl]

Step 1: Preparation of 4-Fluoro-4-(3-hydroxyphenyl)piperidine Hydrochloride. This material was prepared from the catalytic hydrogenation of 4-fluoro-4-(3-benzyloxyphenyl)piperidine hydrochloride as described in described Step 4 of Example 6. This afforded 4-(3-hydroxyphenyl)-4-fluoropiperidine hydrochloride in 76% overall yield.

$^1$H NMR (CD$_3$OD): δ=7.14 (t, J=7.8 Hz, 1H), 6.75 (bd, J=7.8 Hz, 1H), 6.71 (m, 1H), 6.67 (td, J=8.1, 1.6 Hz, 1H), 3.50 (bd, J=12.6 Hz, 2H), 3.14 (m, 1H), 2.84 (tt, J=12.0, 3.6 Hz, 1H), 2.07 (bd, J=15.0 Hz, 2H) and 1.94 ppm (m, 2H).

Step 2: Preparation of 4-Fluoro-4-(3-hydroxyphenyl)-1-(trans-3-phenylcyclopropyl-methyl)piperidine Hydrochloride To a suspension of 4-fluoro-4-(3-hydroxyphenyl)piperidine hydrochloride (100 mg, 0.43 mmol) in THF (3 mL) was added triethylamine (108 mg, 1.07 mmol) and the resulting mixture cooled in an ice bath. A solution of trans-2-phenylcyclopropanecarbonyl chloride (194 mg, 1.07 mmol) in THF (2 mL) was added slowly via syringe over a period of 5 minutes. The reaction was then stirred for additional 3 hours during which time it was allowed to warm to room temperature. The reaction was then quenched by pouring into water (20 mL) and the mixture extracted with ethyl acetate (2×20 mL). The extracts were dried over magnesium sulfate and filtered. The filtrate was then concentrated to afford crude 3-[4-fluoro-1-(trans-2-phenylcyclopropanecarbonyl)piperidin-4-yl]-phenyl trans-2-phenylcyclopropane carboxylate as a viscous clear oil. This oil was dissolved in THF (5 mL) and a 65 wt % solution of vitride in toluene (1.35 mL, 4.50 mmol) added. The resulting mixture was then stirred at room temperature for 2 hours. After this time the reaction was heated to 60° C. for a further 2 hours then cooled back to room temperature. The reaction was then cooled in an ice-bath and ethyl acetate (10 mL) slowly added. The resulting mixture was then slowly added to 10% hydrochloric acid solution (25 mL) and the mixture rapidly stirred for 1 hour. The reaction mixture was then adjusted to pH 8 by the addition of solid sodium bicarbonate and the layers separated. The aqueous was extracted with ethyl acetate (3×10 mL) and the combined organics dried over magnesium sulfate. Subsequent filtration and concentration afforded a brown oil. This material was treated with 10% methanolic hydrogen chloride (5 mL) and re-concentrated. The resulting oil was triturated with 1:1 ethyl acetate/acetone to afford a light brown solid. This solid was isolated by filtration and dried on the pump overnight. This afforded the title compound in 11% overall yield as a tan colored solid.

$^1$H NMR (CD$_3$OD): δ=7.24 (m, 2H), 7.11 (m, 4H), 6.91 (bd, J=7.8 Hz, 1H), 6.71 (m, 1H), 6.73 (bd, J=7.0 Hz, 1H), 3.98 (bs, 1H), 3.64 (m, 1H), 3.55 (bd, J=9.7 Hz, 1H), 3.34 (bd, J=7.6 Hz, 2H), 3.19 (m, 1H), 2.85 (bs, 1H), 2.52 (m, 1H), 2.27 (bs, 2H), 2.10 (bs, 1H) 1.51 (bs, 1H) and 1.30 ppm (m, 2H).

Example 25

Preparation of Morphine-3-{2-Benzyl-3-[4-(3-Methoxyphenyl)-4-fluoropiperidin-1-yl]propionate}

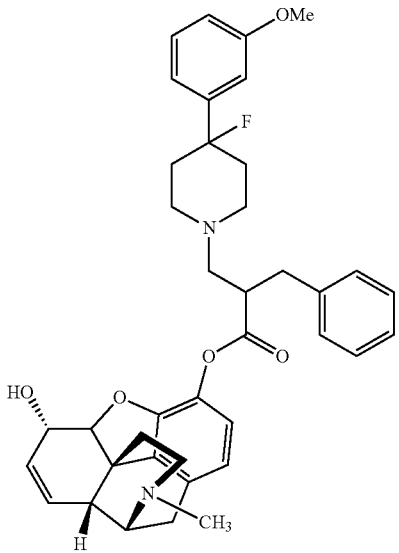

Step 1: Preparation of Morphine-3-(2-Benzylacrylate)

To a solution of morphine hydrochloride (1 equivalent) in water (100 volume equivalents) is added sodium bicarbonate (30 equivalents) and the resulting mixture stirred rapidly. 2-Benzylacryloyl chloride (5 equivalents) is then added dropwise manner and the reaction mixture stirred overnight. After this time the reaction mixture is extracted several times with ethyl acetate and the combined extracts washed with 5% aqueous sodium carbonate and then with water. The organics are then dried over magnesium sulfate, filtered and concentrated under reduced pressure. The crude product obtained is then purified by column chromatography to afford morphine-3-(2-benzylacrylate).

Step 2: Preparation of Morphine-3-{2-Benzyl-3-[4-(3-methoxyphenyl)-4-fluoropiperidin-1-yl]propionate} To a solution of morphine-3-(2-benzylacrylate) (1.5 equivalents) in methanol (30 volume equivalents) is added 4-(3-methoxyphenyl)-4-fluoropiperidine hydrochloride (1.0 equivalents) followed by sodium bicarbonate (10 equivalents) and the resulting suspension stirred at room temperature for 72 hours. After this time the reaction is filtered and the filtrate concentrated under reduced pressure. The resulting crude material is purified by silica gel column chromatography to afford morphine-3-{2-benzyl-3-[4-(3-Methoxyphenyl)-4-fluoropiperidin-1-yl]propionate.

Example 26

Assay of Compounds for Affinity for the Mu Opioid Receptor

Compounds of the invention were assayed for affinity for the Mu opioid receptor using the methodology described in Zhang et al. (*J. Pharmacol. Exp. Ther.*, (1998) 286: 136-141). Compounds were assessed in human recombinant (HEK-293) cells using tritium labeled diprenorphine (0.4 nM) as the specific determinant and non-specific binding was assayed with naltrexone (1 μM). Cells were incubated for 120 minutes at 22° C. before isolation and radioactivity determination by scintillation counting. The $IC_{50}$ values (concentration causing a half-maximal inhibition of control specific binding) and Hill coefficients (nH) were determined by non-linear regression analysis of the competition curves generated with mean replicate values using Hill equation curve fitting ($Y=D+[(A-D)/(1+(C/C_{50})^{nH})]$, where Y=specific binding, D=minimum specific binding, A=maximum specific binding, C=compound concentration, $C_{50}=IC_{50}$, and nH=slope factor). The inhibition constants ($K_i$) were calculated using the Cheng-Prusoff equation ($K_i=IC_{50}/(1+(L/K_D))$, where L=concentration of radioligand in the assay, and $K_D$=affinity of the radioligand for the receptor). Each data point was obtained in duplicate and results are the mean value.

TABLE 1

Affinity of Compounds of the Invention for the Mu Opioid Receptor.

| Example | Affinity |
| --- | --- |
| 1 | + |
| 5 | + |
| 11 | +++ |
| 13 | +++ |
| 15 | +++ |
| 17 | ++ |

TABLE 1-continued

Affinity of Compounds of the Invention for the Mu Opioid Receptor.

| Example | Affinity |
| --- | --- |
| 18 | + |
| 19 | + |

Key:
+ 10 μM > Ki > 1 μM
++ 1 μM > Ki > 0.1 μM
+++ Ki < 0.1 μM

The invention claimed is:
1. A compound of formula:

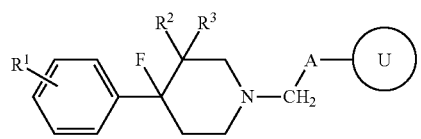

wherein
R¹ is from one to three substituents chosen independently in each occurrence from hydrogen, halogen, halo($C_1$-$C_6$)alkyl, ($C_1$-$C_6$)alkyl, ($C_1$-$C_6$)acyl, ($C_1$-$C_6$)alkoxy($C_1$-$C_6$)alkyl, hydroxy($C_1$-$C_6$)alkyl, heteroaryl, benzenesulfonyl, toluenesulfonyl, hydroxy, ($C_1$-$C_6$)alkoxy, hydroxy($C_1$-$C_6$)alkoxy, halo($C_1$-$C_6$)alkoxy, ($C_1$-$C_6$)oxaalkyl, carboxy, carboxy($C_1$-$C_6$)alkoxy, ($C_1$-$C_6$)alkoxycarbonyl, ($C_1$-$C_6$)alkoxycarbonylamino, carboxamido, ($C_1$-$C_6$)alkylaminocarbonyl, ($C_1$-$C_6$)alkylaminocarbonyloxy, ($C_1$-$C_6$)alkylaminocarbonylamino, cyano, acetoxy, nitro, amino, ($C_1$-$C_6$)alkylamino, di($C_1$-$C_6$)alkylamino, ($C_1$-$C_6$)alkylamino($C_1$-$C_6$)alkyl, di($C_1$-$C_6$)alkylamino($C_1$-$C_6$)alkyl, di($C_1$-$C_6$)alkylamino($C_1$-$C_6$)alkoxy, mercapto, ($C_1$-$C_6$)alkylthio, ($C_1$-$C_6$)alkylsulfonylamino, benzenesulfonylamino, toluenesulfonylamino, ($C_1$-$C_6$)alkylaminosulfonyl, di($C_1$-$C_6$)alkylaminosulfonyl, ($C_1$-$C_6$)alkylsulfinyl, ($C_1$-$C_6$)alkylsulfonyl, ($C_1$-$C_6$)acylamino, aryl, benzyl, heterocyclyl, heterocyclyl($C_1$-$C_6$)alkyl, phenoxy, benzyloxy, heteroaryloxy, hydroxyimino, ($C_1$-$C_6$)alkoxyimino, oxaalkyl, amidino, and guanidino;
R² and R³ are independently chosen from hydrogen and ($C_1$-$C_6$)alkyl;
A is a ($C_1$-$C_8$)alkylene chain wherein one to three methylenes may be optionally replaced by oxygen or —CR⁴R⁵—;
R⁴ and R⁵ are independently chosen from hydrogen, ($C_1$-$C_{10}$)alkyl, halo($C_1$-$C_6$)alkyl, ($C_1$-$C_6$)acyl, hydroxy($C_1$-$C_6$)alkyl, hydroxy, ($C_1$-$C_6$)alkoxy, hydroxy($C_1$-$C_6$)alkoxy, halo($C_1$-$C_6$)alkoxy, ($C_1$-$C_6$)oxaalkyl, carboxy, ($C_1$-$C_6$)alkoxycarbonyl, ($C_1$-$C_6$)alkoxycarbonylamino, carboxamido, ($C_1$-$C_6$)alkylaminocarbonyl, amino, ($C_1$-$C_6$)alkylamino, di($C_1$-$C_6$)alkylamino, aryl, benzyl, heterocyclyl, heterocyclyl($C_1$-$C_6$)alkyl, phenoxy, benzyloxy and heteroaryloxy; and
U is chosen from optionally substituted ($C_3$-$C_8$)carbocycle, thiophene and furanyl.
2. A compound according to claim 1 of formula

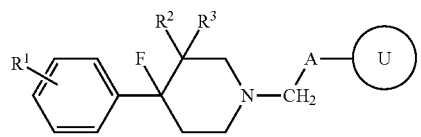

wherein
R¹ is chosen from hydrogen, halogen, hydroxy, ($C_1$-$C_6$) alkoxy, amino, carboxy($C_1$-$C_6$)alkoxy, toluenesulfonylamino, ($C_1$-$C_6$)alkylsulfonylamino, ($C_1$-$C_6$)alkylaminocarbonyloxy, ($C_1$-$C_6$)alkylaminocarbonylamino and hydroxy($C_1$-$C_6$)alkoxy;
R² and R³ are independently chosen from hydrogen and ($C_1$-$C_6$)alkyl;
A is chosen from —C(R⁴R⁵)—, —C(R⁴R⁵)C(R⁶R⁷)—, —C(R⁴R⁵)O—, —C(R⁴R⁵)C(R⁶R⁷)C(R⁸R⁹)— and —C(R⁴R⁵)C(R⁶R⁷)O—;
U is chosen from optionally substituted ($C_3$-$C_8$)carbocycle, thiophene and furanyl; and
R⁴, R⁵, R⁶, R⁷, R⁸ and R⁹ are independently chosen from hydrogen, hydroxy, carboxy, ($C_1$-$C_{10}$)alkyl, aryl and benzyl, with the proviso that no more than two of R⁴, R⁵, R⁶, R⁷, R⁸ and R⁹ are other than hydrogen.

3. A compound according to claim 2 wherein A is chosen from —C(R⁴R⁵)C(R⁶R⁷)—, —C(R⁴R⁵)O— and —C(R⁴R⁵)C(R⁶R⁷)C(R⁸R⁹)—.

4. A compound according to claim 3 wherein A is chosen from —C(R⁴R⁵)C(R⁶R⁷)— and —C(R⁴R⁵)O—.

5. A compound according to claim 2 wherein U is chosen from optionally substituted phenyl, cyclohexyl, thiophene and furanyl.

6. A compound according to claim 5 wherein U is optionally substituted with at least one substituent selected from the group consisting of hydrogen, halogen, halo($C_1$-$C_6$)alkyl, ($C_1$-$C_6$)alkyl, cyano, acetoxy, ($C_1$-$C_6$)alkylthio, aryl, aryl($C_1$-$C_6$)alkyl, heterocyclyl, heterocyclyl($C_1$-$C_6$)alkyl, phenoxy, benzyloxy, aryloxy and heteroaryloxy.

7. A compound according to claim 2 wherein R¹ is chosen from hydrogen, chlorine, fluorine, hydroxy, amino, toluenesulfonylamino, methylsulfonylamino, ethylaminocarbonyloxy, t-butylaminocarbonylamino, carboxymethoxy and hydroxyethoxy.

8. A compound according to claim 7 wherein R¹ is chosen from chlorine in the para position and hydroxy in the para or meta position, each position relative to the attachment of the piperidine.

9. A compound according to claim 2 wherein R² is hydrogen and R³ is chosen from hydrogen and methyl.

10. A compound according to claim 1
wherein
R¹ is chosen from hydrogen, chlorine, fluorine, hydroxy, amino, toluenesulfonylamino, methylsulfonylamino, ethylaminocarbonyloxy, t-butylaminocarbonylamino, carboxymethoxy and hydroxyethoxy;
R² and R³ are independently chosen from hydrogen and ($C_1$-$C_6$)alkyl;
A is chosen from —C(R⁴R⁵)C(R⁶R⁷)—, —C(R⁴R⁵)O— and —C(R⁴R⁵)C(R⁶R⁷)C(R⁸R⁹)—;
U is chosen from optionally substituted phenyl, cyclohexyl, thiophene and furanyl; and
R⁴, R⁵, R⁶, R⁷, R⁸ and R⁹ are independently chosen from hydrogen, hydroxy, carboxy, ($C_1$-$C_{10}$)alkyl, aryl and benzyl, with the proviso that no more than two of R⁴, R⁵, R⁶, R⁷, R⁸ and R⁹ are other than hydrogen.

11. A compound according to claim 10
wherein
R¹ is chosen from chlorine in the para position and hydroxy in the para or meta position, each position relative to the attachment of the piperidine;
R² is hydrogen;
R³ is chosen from hydrogen and methyl;
A is chosen from —CH₂CH₂—, —CH₂O—, —CH₂CH₂CH₂—,

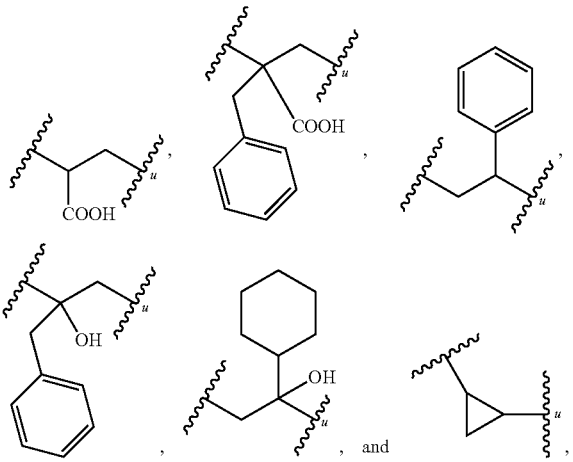

wherein u indicates the point of attachment to U; and
U is chosen from phenyl, cyclohexyl, thiophene and furanyl.

12. A compound of claim 11 selected from

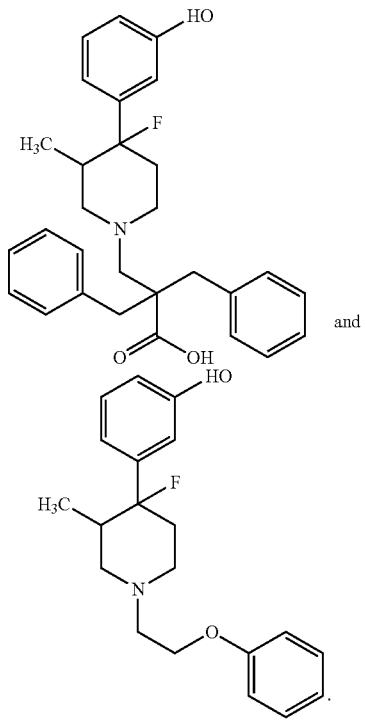

13. A pharmaceutical composition comprising at least one compound of claim 1 and a pharmaceutically acceptable carrier.

14. A diagnostic composition comprising a pharmaceutical carrier suitable for injection and at least one compound selected from claim 1, wherein the 4-fluorine is [¹⁸F]-fluoro.

15. A composition according to claim 14 for positron emission tomography of prostate, blood, lymph, ovary, cervix, bladder, breast or brain.

* * * * *